(12) United States Patent
Hartman et al.

(10) Patent No.: US 9,017,980 B2
(45) Date of Patent: *Apr. 28, 2015

(54) VARIANT FORMS OF URATE OXIDASE AND USE THEREOF

(71) Applicant: Crealta Pharmaceuticals LLC, Lake Forest, IL (US)

(72) Inventors: Jacob Hartman, Holon (IL); Simona Mendelovitz, Ramat Aviv (IL)

(73) Assignee: Crealta Pharmaceuticals LLC, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/972,167

(22) Filed: Aug. 21, 2013

(65) Prior Publication Data

US 2013/0330803 A1  Dec. 12, 2013

Related U.S. Application Data

(60) Continuation of application No. 13/461,170, filed on May 1, 2012, now Pat. No. 8,541,205, which is a division of application No. 11/918,297, filed as application No. PCT/US2006/013660 on Apr. 11, 2006, now Pat. No. 8,188,224.

(60) Provisional application No. 60/670,573, filed on Apr. 11, 2005.

(51) Int. Cl.
*C12N 9/00* (2006.01)
*C12N 9/06* (2006.01)
*A61K 47/48* (2006.01)

(52) U.S. Cl.
CPC ........ *C12N 9/0048* (2013.01); *A61K 47/48215* (2013.01); *C12N 9/0046* (2013.01); *C12Y 107/03003* (2013.01)

(58) Field of Classification Search
CPC ................................. C12N 9/0048; C12N 9/06
USPC ................ 435/191, 9.1, 89, 252.33, 320.1, 9
See application file for complete search history.

(56) References Cited

U.S. PATENT DOCUMENTS

| | | | |
|---|---|---|---|
| 3,451,996 A | 6/1969 | Sumyk et al. |
| 3,616,231 A | 10/1971 | Bergmeyer et al. |
| 3,931,399 A | 1/1976 | Bohn et al. |
| 1,141,973 A | 2/1979 | Balazs |
| 4,169,764 A | 10/1979 | Takezawa et al. |
| 4,179,337 A | 12/1979 | Davis et al. |
| 4,297,344 A | 10/1981 | Schwinn et al. |
| 4,301,153 A | 11/1981 | Rosenberg |
| 4,312,979 A | 1/1982 | Takemoto et al. |
| 4,317,878 A | 3/1982 | Nakanishi et al. |
| 4,421,650 A | 12/1983 | Nagasawa et al. |
| 4,425,431 A | 1/1984 | Takemoto et al. |
| 4,445,745 A | 5/1984 | Cartesse |
| 4,460,575 A | 7/1984 | d'Hinterland et al. |
| 4,460,683 A | 7/1984 | Gloger et al. |
| 4,485,176 A | 11/1984 | Bollin, Jr. et al. |
| 4,753,796 A | 6/1988 | Moreno et al. |
| 4,766,106 A | 8/1988 | Katre et al. |
| 4,797,474 A | 1/1989 | Patroni et al. |
| 4,847,325 A | 7/1989 | Shadle et al. |
| 4,917,888 A | 4/1990 | Katre et al. |
| 4,945,086 A | 7/1990 | Benitz et al. |
| 4,966,963 A | 10/1990 | Patroni |
| 4,987,076 A | 1/1991 | Takashio et al. |
| 4,992,531 A | 2/1991 | Patroni et al. |
| 5,008,377 A | 4/1991 | Patroni et al. |
| 5,010,183 A | 4/1991 | Macfarlane |
| 5,283,317 A | 2/1994 | Saifer et al. |
| 5,286,637 A | 2/1994 | Veronese et al. |
| 5,362,641 A | 11/1994 | Fuks et al. |
| 5,382,518 A | 1/1995 | Caput et al. |
| 5,428,128 A | 6/1995 | Mensi-Fattohi et al. |
| 5,458,135 A | 10/1995 | Patton et al. |
| 5,468,478 A | 11/1995 | Saifer et al. |
| 5,529,915 A | 6/1996 | Phillips et al. |
| 5,541,098 A | 7/1996 | Caput et al. |
| 5,567,422 A | 10/1996 | Greenwald |
| 5,612,460 A | 3/1997 | Zalipsky et al. |
| 5,624,903 A | 4/1997 | Muller et al. |
| 5,633,227 A | 5/1997 | Muller et al. |
| 5,637,749 A | 6/1997 | Greenwald et al. |
| 5,643,575 A | 7/1997 | Martinez et al. |
| 5,653,974 A | 8/1997 | Hung et al. |

(Continued)

FOREIGN PATENT DOCUMENTS

| | | |
|---|---|---|
| CA | 2193993 A1 | 1/1996 |
| CN | 1322141 A | 11/2001 |

(Continued)

OTHER PUBLICATIONS

Susumu Tsunasawa et al., "Amino-terminal Processing of Mutant Forms of Yeast Iso-1-cytochrome c, The Specificities of Methionine Aminopeptidase and Acetyltransferase" The Journal of Biological Chemistry, vol. 260, No. 9, Issue of May 10, pp. 5382-5391, 1985.

Ph.-Herve Hirel et al.; "Extent of N-terminal Methionine Excision from *Escherichia coli* Proteins is Governed by the Side-Chain Length of the Penultimate Amino Acid," Proc. Natl. Acad. Sci. USA; vol. 86, pp. 8247-8251, Nov. 1989, Biochemistry.

Sundy, J.S. et al., A Phase I Study of Pegylated-Uricase (Puricase®) in Subjects with Gout, Arthritis Rheum. 2004 vol. 50, supplement 9, S337-338.

(Continued)

*Primary Examiner* — Julie Ha

(74) *Attorney, Agent, or Firm* — Lando & Anastasi LLP

(57) ABSTRACT

Genetically modified proteins with uricolytic activity are described. Proteins comprising truncated urate oxidases and methods for producing them, including PEGylated proteins comprising truncated urate oxidase are described.

17 Claims, 8 Drawing Sheets

(56) References Cited

U.S. PATENT DOCUMENTS

| | | | |
|---|---|---|---|
| 5,766,897 A | 6/1998 | Braxton | |
| 5,811,096 A | 9/1998 | Aleman et al. | |
| 5,880,255 A | 3/1999 | Delgado et al. | |
| 5,919,455 A | 7/1999 | Greenwald et al. | |
| 5,929,231 A | 7/1999 | Malkki et al. | |
| 5,932,462 A | 8/1999 | Harris et al. | |
| 5,948,668 A | 9/1999 | Hartman et al. | |
| 5,955,336 A | 9/1999 | Shigyo et al. | |
| 6,201,110 B1 | 3/2001 | Olsen et al. | |
| 6,211,341 B1 | 4/2001 | Zeelon et al. | |
| 6,468,210 B1 | 10/2002 | Iliff | |
| 6,475,143 B2 | 11/2002 | Iliff | |
| 6,524,241 B2 | 2/2003 | Iliff | |
| 6,527,713 B2 | 3/2003 | Iliff | |
| 6,569,093 B2 | 5/2003 | Iliff | |
| 6,576,235 B1 | 6/2003 | Williams et al. | |
| 6,608,892 B2 | 8/2003 | Shaffer et al. | |
| 6,783,965 B1 | 8/2004 | Sherman et al. | |
| 6,913,915 B2 | 7/2005 | Ensor et al. | |
| 7,056,713 B1 * | 6/2006 | Hershfield et al. | 435/189 |
| 7,723,089 B2 | 5/2010 | Williams et al. | |
| 7,927,589 B2 | 4/2011 | Williams et al. | |
| 7,927,852 B2 | 4/2011 | Sherman et al. | |
| 8,067,553 B2 | 11/2011 | Williams et al. | |
| 8,148,123 B2 | 4/2012 | Hartman et al. | |
| 8,188,224 B2 | 5/2012 | Hartman et al. | |
| 8,541,205 B2 | 9/2013 | Hartman et al. | |
| 8,618,267 B2 | 12/2013 | Williams et al. | |
| 2002/0010319 A1 | 1/2002 | Ansaldi et al. | |
| 2003/0082786 A1 | 5/2003 | Ensor et al. | |
| 2003/0166249 A1 | 9/2003 | Williams et al. | |
| 2005/0014240 A1 | 1/2005 | Sherman et al. | |
| 2006/0188971 A1 | 8/2006 | Hershfield et al. | |
| 2007/0274977 A1 | 11/2007 | Hartman et al. | |
| 2008/0159976 A1 | 7/2008 | Hartman et al. | |
| 2009/0209021 A1 | 8/2009 | Hartman et al. | |
| 2009/0317889 A1 | 12/2009 | Fischer et al. | |
| 2010/0323423 A1 | 12/2010 | Williams et al. | |
| 2011/0287466 A1 | 11/2011 | Sherman et al. | |
| 2012/0149083 A1 | 6/2012 | Williams et al. | |

FOREIGN PATENT DOCUMENTS

| | | |
|---|---|---|
| CN | 1322243 A | 11/2001 |
| DE | 279 486 A1 | 6/1990 |
| EP | 055188 | 5/1984 |
| EP | 0408 461 A | 1/1991 |
| EP | 1100542 A2 | 5/2001 |
| JP | 55-99189 | 7/1980 |
| JP | 62-55079 | 3/1987 |
| JP | 03-148298 | 6/1991 |
| JP | 09-154581 | 6/1997 |
| JP | H10-500565 A | 1/1998 |
| JP | H10-502360 A | 3/1998 |
| JP | 1999-075876 | 3/1999 |
| JP | H11-075876 | 3/1999 |
| JP | 2002-522399 A | 7/2002 |
| JP | 2002-524053 A | 8/2002 |
| JP | 2008505656 A | 2/2008 |
| KR | 333148 | 9/1994 |
| KR | 318706 | 4/1997 |
| KR | 365606 | 3/1998 |
| KR | 488848 | 2/2000 |
| KR | 10-0369838 B1 | 1/2003 |
| KR | 369838 | 1/2003 |
| WO | WO8604145 A1 | 7/1986 |
| WO | 9419470 A1 | 9/1994 |
| WO | WO 94/19007 A1 | 9/1994 |
| WO | WO94/23735 | 10/1994 |
| WO | WO9511987 A1 | 5/1995 |
| WO | 9525785 A1 | 9/1995 |
| WO | 9601274 A1 | 1/1996 |
| WO | WO96/23064 | 8/1996 |
| WO | 9808873 A1 | 3/1998 |
| WO | WO 98/31383 A1 | 7/1998 |
| WO | WO 00/07629 A2 | 2/2000 |
| WO | WO 00/08196 A3 | 2/2000 |
| WO | WO 01/59078 A2 | 8/2001 |
| WO | 03011211 A2 | 2/2003 |
| WO | WO03045436 A1 | 6/2003 |

OTHER PUBLICATIONS

Sundy, J.S. et al., A Phase I Study of Pegylated-Uricase (Puricase®) in Subjects with Gout, presented at American College of Rheumatology Annual Scientific Meeting on Oct. 16-21, 2004 at San Antonio, TX, Poster 807.

Ganson, N.J. et al., Antibodies to Polyethylene Glycol (PEG) during Phase I Investigation of PEG-Urate Oxidase (PEG-uricase; Puricase®) for Refractory Gout, Arthritis Rheum. 2004 vol. 50, supplement 9, S338.

Ganson, N.J. et al., Antibodies to Polyethylene Glycol (PEG) during Phase I Investigation of PEG-Urate Oxidase (PEG-uricase; Puricase®) for Refractory Gout, presented at American College of Rheumatology Annual Scientific Meeting on Oct. 16-21, 2004 at San Antonio, TX, Poster 808.

Baraf H. et al., Sep. 2005, "Arthritis & Rheumatism" in The Official Journal of the American College of Rheumatology, Abstract Supplement, vol. 52, No. 9, p. S105.

Baraf H. et al., Resolution of Tophi With Intravenous PEG-uricase in Refractory Gout, presented at American College of Rheumatology 2005 Annual Scientific Meeting on Nov. 13-17, 2005 at San Diego, CA, Poster 194.

Sundy, J.S. et al., A Phase 2 Study of Multiple Doses of Intravenous Polyethylene Glycol (PEG)-uricase in Patients with Hyperuricemia and Refractory Gout, presented at American College of Rheumatology 2005 Annual Scientific Meeting on Nov. 13-17, 2005 at San Diego, CA, #1836.

Kelly, S. J., M. Delnomdedieu, et al. (2001) as "Diabetes insipidus in uricase-deficient mice: A model for evaluating therapy with poly(ethylene glycol)-modified uricase." in J Am Soc Nephrol 12: 1001-1009.

Lee et al., (Sep. 2005) as "Arthritis & Rheumatism" in The Official Journal of the American College of Rheumatology, Abstract Supplement, vol. 52, No. 9, p. S105.

Office Action dated Jan. 26, 2010, U.S. Appl. No. 11/918,296, filed Dec. 11, 2008, Inventor Jacob Hartman.

Office Action dated Oct. 30, 2009, U.S. Appl. No. 11/539,475, filed Oct. 6, 2006, Inventor Jacob Hartman.

Office Action dated Jun. 25, 2009, U.S. Appl. No. 11/539,475, filed Oct. 6, 2006, Inventor Jacob Hartman.

Office Action dated Oct. 30, 2009, U.S. Appl. No. 11/899,688, filed Sep. 7, 2007, Inventor Jacob Hartman.

Cristina Delgado, Gillian E. Francis, and Derek Fisher; "The Uses and Properties of PEG-Linked Proteins," Molecular Cell Pathology Laboratory, Royal Free Hospital School of Medicine, London, UK., Critical Review in Therapeutic Drug Carrier Systems, 9 (3, 4): 249-304 (1992).

Arie Ben-Bassat, Keith Bauer, Sheng-Yung Chang, Ken Myambo, Albert Boosman, Shing Chang, "Processing of the Initiation Methionine from Proteins: Properties of the *Escherichia coli* Methionine Aminopeptidase and its Gene Structure," Journal of Bacteriology, American Society for Microbiology, Feb. 1987, vol. 169, No. 2, pp. 751-757.

Montalbini, P. et al., Isolation and characterization of uricase from bean leaves and its comparison with uredospore enzymes, Plant Sci. 147:139-147, Elsevier Science Ireland Ltd. (May 1999).

Abuchowski, A., et al., "Reduction of Plasma Urate Levels in the Cockerel with Polyethylene Glycol-Uricase," J. Pharmacol. Exp. Ther. 219:352-354, The American Society for Pharmacology and Experimental Therapeutics (1981).

Alvares, K., et al., "The Nucleotide Sequence of a Full Length cDNA Clone Encoding Rat Liver Urate Oxidase," Biodiem. Bibphys. Res. Commun. 158:991-995, Academic Press, Inc. (1989).

Alvares, K., et al., "Rat urate oxidase produced by recombinant baculovirus expression: Formation of peroxisome crystallized core-like structures," Proc. Natl. Acad. Sci. USA 89:4908-4912, National Academy of Sciences (1992).

(56) References Cited

OTHER PUBLICATIONS

Braun, A. and Alsenz, J., "Development and Use of Enzyme-Linked Immunosorbent Assays (ELISA) for the Detection of Protein Aggregates in Interferon-Alpha (IFN-α) Formulations," Pharm. Res. 14:1394-1400, Plenum Publishing Corporation (Oct. 1997).
Braun, A., et al. "Protein Aggregates Seem to Play a Key Role Among the Parameters Influencing the Antigenicity of Interferon Alpha (IFN-α) in Normal and Transgenlc Mice," Pharm. Res. 14:1472-1478, Plenum Publishing Corporation (Oct. 1997).
Burnham, N.L., "Polymers for delivering peptides and proteins," Am. J. Hosp. Pharm. 51:210-218, American Society of Hospital Pharmacists, Inc. (1994).
Caliceti, P., et al., "Biopharmaceutical Properties of Uricase Conjugated to Neutral and Amphiphilic Polymers," Biodonjugate Cheat. 10:639-646, American Chemical Society (Jul.-Aug. 1999).
Chen, R.H.-L., et al., "Properties of Two Urate Oxidases Modified by the Covalent Attachment of Poly(Ethylene Glycol)," Biochem. Biophys. Acta 660:293-298, Elsevier/North Holland Biomedical Press (1981).
Chua, C.C., et al., "Use of Polyethylene Glycol-Modified Uricase (PEG-Uricase) to Treat Hyperuricemia in a Patient with Non-Hodgkin Lymphoma," Ann. Intern. Med. 109:114-117, American College of Physicians (1988).
Colloc'h, N., et al., "Crystal Structure of the protein drug urate oxidase-inhibitor complex at 2.05 A resolution," Nature Struct. Biol. 4:947-952, Nature Publishing Company (Nov. 1997).
Conley, T.G., and Priest, D.G., "Thermodynamics and Stoicheiometry of the Binding of Substrate Analogues to Uricase," Biochem. J. 187:727-732, The Biochemical Society (1980).
Davis, F.F., et al., "Enzyme-Polyethylene Glycol Adducts: Modified Enzymes with Unique Properties," in: Enzyme Engineering, vol. 4, Braun, G.B., et al., eds., Plenum Press, New York, pp. 169-173 (1978).
Davis, S., et al., "Hypouricaemic Effect of Polyethyleneglycol Modified Urate Oxidase," Lancet 2:281-283, Lancet Publishing Group (1981).
Donadio, D., et al., "Manifestation de type anaphylactique après injection intra-veineuse d'urate-oxydase chez uh enfant asthmatique atteint de leucèmie aiguë," La Nouv. Presse Med. 10:711-712, Masson (1981).
Unverified English language partial translation of Donadio, D., et al., "Anaphylaxis-like manifestations after intravenous injection of urate oxidase in an asthmatic child with acute leukemia," La Nouv. Presse Med. 10:711-712, Masson (1981) (Document NPL15).
Fam, A.G., "Strategies and Controversies in the Treatment of Gout and Hyperuricaemia," Bailière's Clinical Rheumatology 4:177-192, Ballière Tindall (1990).
Fridovich, I., "The Competitive Inhibition of Uricase by Oxonate and by Related Derivatives of s-Triazines," J. Biol. Chem. 240:2491-2494, American Society for Biochemistry and Molecular Biology (1965).
Fuertges, F., and Abuchowski, A., "The Clinical Efficacy of Poly(Ethylene Glycol)-Modified Proteins," J. Control. Release 11:139-148, Elsevier Science (1990).
Fujita, T., et al., "Tissue Distribution of 111 In-Labeled Uricase Conjugated with Charged Dextrans and Polyethylene Glycol," J. Pharmacobio-Dyn. 14:623-629, Pharmaceutical Society of Japan (1991).
Greenberg, M.L. and Hershfield, M.S., "A Radiochemcial-High-Performance Liquid Chromatographic Assay for Urate Oxidase in Human Plasma," Anal. Biochem. 176:290-293, Academic Press, Inc. (1989).
Hande, K.R., et al., "Severe Allpurinol Toxicity. Description and Guidelines for Prevention in Patients with Renal Insufficiency," Am. J. Med. 76:47-56, Excerpta Medica (1984).
Hedlund, L.W., et al., "Magnetic Resonance Microscopy of Toxic Renal Injury Induced by Bromoethylamine in Rats," Fundain. Appl. Toxicol. 16:787-797, Academic Press (1991).

Henney, C.S. and Ellis, E.F., "Antibody Production to Aggregated Human γG-Globulin in Acquired Hypogammaglobulinemia," New Engl. J. Med. 278:1144-1146, Massachusetts Medical Society (1968).
Herbst, R et al., "Folding of Firefly (*Photinus pyralis*) Luciferase: Aggregation and Reactivation of Unfolding Intermediates," Biochem. 37:6586-6597, American Chemical Society (May 1998).
Hershfield, M.S., et al., "Use of Site-Directed Mutagenesis to Enhance the Epitope-shielding Effect of Covalent Modifitation of Proteins with Polyethylene Glycol," Proc. Natl. Acad. Sci. USA 88:7185-7189, Natinal Academy of Sciences (1991).
Ishino, K. and Kudo, S., "Proteins Concentration Dependence on Aggregation Behavior and Properties of Soybean 7S and 11S Globulins during Alkali-treatment," Agric. Biol. Chem. 44:1259-1266, Agricultural Chemical Society of Japan (1980).
Ito, M., et al., "Identification of an Amino Acid Residue Involved in the Substrate-binding Site of Rat Liver Uricase by Site-directed Mutagenesis," Biochem. Biophys. Res. Commun. 187:101-107, Academic Press (1992).
Kahn, K., and Tipton, P.A., "Kinetic Mechanism and Cofactor Content of Soybean Root Nodule Rate Oxidase," Biochemistry 36:4731-4738, American Chemical Society (Apr. 1997).
Kelly, S.J., et al., "Diabetes Insipidus in Urlcase-Deficient Mice: A Model for Evaluating Therapy with Poly (Ethylene Glycol)-Modified Uricase," J. Am,. Soc. Nephrol. 12:1001-1009, Lippincott Williams & Wilkins (May 2001).
Kito, M., et al., "A Simple and Efficient Method for Preparation of Monomethoxopolyethylene Glycol Activated with p-Nitrophenylchlorformate and Its Application to Modiciation of L-Asparanginase," J. Clin. Biochem. Nutr. 21:101-111, Institute of Applied Biochemistry (1996).
Kunitanl, M., et al., "On-line characterization of polyethylene glycol-modified proteins," J. Chromat. 588:125-137, Elsevier Science Publishers B.V. (1991).
Kunitani, M., et al., "Classical light scattering quantitaiton of protein aggregates: off-line spectroscopy versus HPLC detection," J. Pharm. Blomed. Anal. 16:573-586, Elsevier Science B.V. (Dec. 1997).
Leach, M. et al., "Efficacy of Urate Oxidase (Uricozyrne) in Tumour Lysis Induced. Urate Nephropathy," Clin. Lab. Haematol. 20:169-172, Blackwell Scientific Publications (Jun. 1998).
Lee, C.C., et al., "Generation of cDNA Probes Directed by Amino Acid Sequence: Cloning of Urate Oxidase," Science 239:1288-1291, American Association for th eAdvancement of Science (1988).
Legoux, R. et al., "Cloning and Expression in *Escherichia coli* of the Gene Encoding *Aspergillus flavus* Urate Oxidase ," J. Biol. Chem. 267:8565-8570, American Society for Biochemistry and Molecular Biology (1992).
Madmoud, H.H., et al., "Advances in the Management of Malignancy-Associated Hyperuricaemia," Br. J. Cancer (Supplement 4) 77:18-20, Churchill Livingstone (Jun. 1998).
Mahler, H.R., et al., "Studies of Uricase, I. Preparation, Purification, and Properties of a Cuproprotein," J. Biol. Chem. 216:625-641, American Society for Biochemistry and Molecular Biology (1955).
Mourad G. et al., Presse Med. 1984, 13 (42):2585.
Malakhova, E.A., et al., "Kinetic Properties of Bacterial Urate Oxidase Entrapped in Hydrated Reversed Micelles," Biologicheskie Membrany 8:453-459, Nauka (1991).
Mirua, S., et al., "Urate Oxidase in Imported into Peroxisomes Recognizing the C-terminal SKL Motif of Proteins," Eur. J. Biochem. 223:141-146, Blackwell Science Ltd. (1994).
Monkarsh, S.P., et al., "Positional Isomers of Monopegylated Interferon α-2a: Isolation, Characterization, and Biological Activity ," Analytical Biochemistry 247:434-440, Academic Press (1997).
Montalbini, P., et al., "Uricase form leaves: its purification and characterization from three different higher plants," Planta 202:277-283, Springer-Vertag (Jun. 1997).
Moore, W.V. and Leppert, P., "Role of Aggregated Human Growth Hormone (hGH) in Development of Antibodies to hGH," J. Clin. Endocrinol. Metab. 51:691-697, The Endocrine Society (1980).
Nishida, Y., et al., "Hypouricaemic effect after oral administration in chickens of polyethylene glycol-modified uricase entrapped in liposomes," J. Pharm. Pharmacol. 36:354-355; Pharmaceutical Press (1984).

(56) References Cited

OTHER PUBLICATIONS

Nishimura, H., et al., "Modification of Yeast Uricase with Polyethlene Glycol: Disappearance of Binding Ability towards Anti-Uricase Serum," Enzyme 24:261-264, Karger (1979).
Nishimura, H., et al., "Improved Modification of Yeast Uricase with Polyethylene Glycol, Accompanied with Nonimmunoreactivity Towards Anti-Uricase Serum and High Enzymic Activity," Enzyme 26:49-53, Karger (1981).
Nucci, M.L., et al., "The Therapeutic Value of Poly(Ethylene Glycol)-Modified Proteins," Adv. Drug Deliv. Rev. 6:133-151, Elsevier Science Publishers (1991).
Osman, A.M., et al., "Liver Uricase in *Camelus dromedarius*: Purification and Properties," Comp. Biochem. Physiol. 94B:469-474, Pergamon Press Plc. (1989).
Palleroni, A.V., et al., "Interferon immunogenicity: Preclinical Evaluation of Interferon-α2a," J. Interferon Cyto. Res. 17:S23-527, Mary Ann Liebert, Inc. (Jul. 1997).
"PEG-Uricase BioTechnology General, Duke Univeitity, Mountain View licensing agreement," R&D Focus Drug News, Accession No. 1998-2984, available on Datastar File IPNR/IPNA, (Aug. 1998).
Porstmann, B., et al., "Companion of Chromogens for the Determination of Horseradish Peroxidase as a Marker-in Enzyme Immunoassay," J. Clin. Chem. Clin. Biochem. 19:435-439, Walter de Gruyter & Co. (1981).
Pui, C-H., et al., "Urate oxidase in prevention and treatment of hyperuricemia associated with lymphoid malignancies," Leukemia 11:1813-1816, Stockton Press (Nov. 1997).
Saifer, M.G.P., et al., "Plasma Clearance and Immunologic Properties of Long-Acting Superoxide Dismutase Prepared Using 35,000 to 120,000 Dalton Poly-Ethylene Glycol," in: Free Radicals in Diagnostic Medicine, Armstrong, D., ed., Plenum Press, New York, NY, pp. 377-387 (1994).
Saifer, M.G.P., et al., "Improved Conjugation of Cytokines Using High Molecular Weight Poly(ethylene glycol): PEG-GM-CSF as a Prototype," Polymer Prepr. 38:576-577, American Chemical Society (Apr. 1997).
Sartore, L., et al., "Enzyme Modification by MPEG with an Amino Acid or Peptide as Spacer Arms," Appl. Biochem. Biotechnol. 27:45-54, Humana Press (1991).
Savoca, K.V., et al., "Induction of Tolerance in Mice by Uricase and Monomethoxypolyethylene Glycol-Modified Uricase," Int. Archs. Allergy appl. Immun. 75:58-67, Karger (1984).
Shearwater Polymers Inc., "Functionalized biocompatible Polymers for Research and Pharmaceuticals," in: Shearwater Polymers, Inc., Catalog, pp. 27, 47, and 48. (Jul. 1997).
Sherman, M.P., et al., "Conjugation of High-Molecular Weight Poly(ethyleneglycol) to Cytokines: Granulocyte-Macrophage Colony-Stimulating Factors as Model Substrates," in:ACS Symposium Series 680. Poly(ethylene glycol). Chemistry and Biological Applications, Harris, J.M. and Zalipsky. S., eds., American Chemical Society, Washington, DC, pp. 155-169 (Apr. 1997).
Somack, R., et al., "Preparation of Long-Acting Superoxide Dismutase Using High Molecular Weight Polyethylene Glycol (41,000-72,000 Daltons)," Free Rad. Res. Comms. 12-13:553-562, Harwood Academic Publishers GmbH (1991).
Suzuki, H. and Verma, D.P.S., "Soybean Nodule-Specific Uricase (Nodulin-35) is Expressed and Assembled into a Functional Tetrameric Holoenzyme in *Escherichia coli*," Plant Physiol. 95:384-389, American Society of Plant Physiologists (1991).
Treuheit, M.J., et al., "Inverse Relationship of Protein Concentration and Aggregation," Pharm. Res. 19:511-516, Plenum Publishing Corporation (Apr. 2002).
Tsuji, J.-I., et al., "Studies on Antigenicity of the Polyethylene Glycol (PEG)-Modified Uriacse," Int. J. Immunopharmacol. 7:725-730, Elsevier Science (1985).
Venkataseshan, V.S., et al., "Acute Hyperuricemic Nephropathy and Renal Failure after Transplantation," Nephron 56:317-321, Karger AG (1990).
Veronese, F.M., et al., "Surface Modification of Proteins. Activation of Monomethoxy-Polyethylene Glycols by Phenylchloroformates and Modification of Ribonuclease and Superoxide Dismutase," Appl. Biochem. Biotechnol. 11:141-152, The Humana Press, Inc. (1985).
Veronese, F.M., et al., "New Synthetic Polymers for Enzyme and Liposome Modification," in: ACS Symposium Series 680, Poly(Ethylene Glycol)-Chemistry and Biological Applications, Harris, J.M., and Zalipsky, S., eds., American Chemical Society, Washington, D.C. pp. 182-192 (Apr. 1997).
Wallrath, L.L., et al., "Molecular Characterization of the *Drosophila melanogaster* Urate Oxidase Gene, an Ecdysone-Repressible Gene Expressed Only in the Malpighian Tubules," Molec. Cell. Biol. 10:5114.5127, American Society for Microbiology (1990).
Wang, X., et al., "Rat urate oxidase: cloning and structural analysis of the gene and 5'-flanking region," Gene 97:223-229, Elsevier Science Publishers B.V. (1991).
Wu, X., et al.; "Urate oxidase: Primary structure and evolutionary implications," Proc. Natl. Acad. Sci. USA 86:9412-9416, National Academy of Sciences (1989).
Wu, X., et al., "Two Independent Mutational Events in the Loss of Urate Oxidase during Hominoid Evolution," J. Mol. Evol. 34:78-84, Springer-Verlag (1992).
Wu, X., et al., "Hyperuricemia and urate nephropathy in urate oxidase-deficient mice," Proc. Natl. Acad. Sci, USA 91:742-746, National Academy of Sciences (1994).
Yasuda, Y., et al., "Biochemclal and Biopharmaceutical Properties of Macromolecular Conjugates of Uricase with Dextran Polyethylene Glycol," Chem. Pharm. Bull. 38:2053-2046, Pharmaceutical Society of Japan (1990).
Yeldandi, A.V., et al., "Human Urate Oxidase Gene: Cloning and Partial Sequence Analysis Reveal a Stop Codon within the Fifth Exon," Biochem. Biophys. Res. Commun. 171:641-646, Academic Press (1990).
U.S. Trademark Registration No. 2,246,623, entitled "Puricase," filed Jul. 15, 1997.
NCBI Entrez, GenBank Report, Accession No. NP_446220, Wang, X.D., et al. (Oct. 2004).
S. Sundy et al., Arthritis & Rheumatism, vol. 52, No. 9 (Supplement), Sep. 2005, Abstract Supplement, 2005 annual Scientific Meeting, Nov. 12-17, 2005, San Diego, California; 1836.
Michael A. Becker, Hyperuricemia and Gout, In: The Metabolic and Molecular Bases of Inherited Disease. Edited by Scriver CR, Beaudet AL, Sly WS, Valle D, 8th edn. New York; McGraw-Hill; 2001: 2513-2535.
Terkeltaub RA: Clinical practice. Gout. N. Engl. J. Med. 2003, 349(17):1647-1655.
Wortmann RL et al.: Gout and Hyperuricemia, In: Kelley's Textbook of Rheumatology. Edited by Ruddy S, Harris Ed, Jr., Sledge CB, 6th edn. St. Louis: W.B. Saunders: 2001: 1339-1371.
Li-Yu J et al., Treatment of Chronic Gout . . . Can We Determine When Urate Stores Are Depleted Enough to Prevent Attacks of Gout?, J. Rheumatol 2001, 28(3):577-580.
Perez-Ruiz F. et al., Effect of Urate-Lowering Therapy on the Velocity of Size Reduction of Tophi in Chronic Gout, Arthritis Rheum. 2002, 47(4); 356-360.
Shoji A. et al., A Retrospective Study of the Relationship Between Serum Urate Level and Recurrent Attacks of Gouty Arthritis: Evidence for Reduction of Recurrent Gouty Arthritis With Antihyperuricemic Therapy, ; arthritis Rheum. 2004, 51(3):321-325.
Coiffier B. et al., Efficacy and Safety of Rasburicase (recombinant urate oxidase) for the Prevention and Treatment of Hyperuricemia During Induction Chemotherapy of Aggressive Non-Hodgkin's Lymphoma: Results of the GRAAL1 Study; J. Clin. Oncol. 2003, 21(23):4402-4406.
Goldman SC et al., A Randomized Comparison Between Rasburicase and Allopurinol in Children with Lymphoma or Leukemia at High Risk for Tumor Lysis, Blood 2001, 97 (10): 2998-3303.
Kissel P. et al., Modificaiton of Uricaemia and the Excretion of Uric Acid Nitrogen by an Enzyme of Fungal Origin, Nature 1968, 217: 72-74.
London M. et al., Uricolytic Activity of Purified Uricase in Two Human Beings, Science 1957, 125:937-938.
Montagriac R. et al. Nephrologie 1990, 11 (4):259.
Moolenburgh JD et al., Rasburicase Treatment in Severe Tophaceous Gout: a Novel Therapeutic Option, Clin, Rheumatol 2005: 1-4.

(56) References Cited

OTHER PUBLICATIONS

Richette P. et al., Successful Treatment with Rasburicase of a Tophaceous Gout in a Patient Allergic to Allopurinol, Nature Clinical Practice Rheumatology 2006, 2(6):338-342.
Harris JM et al., Effect of Pegylation on Pharmaceuticals, Nat. Rev. Drug Dlscov. 2003, 2(3):214-221.
Veronese FM et al., Introduction and Overview of Peptide and Protein Pegylation, Advanced Drug Delivery Reviews 2002, 54(4):453-456.
Kelly SJ et al., Diabetes Insipidus in Uricase-Deficient Mice: A Model for Evaluating Therapy with Poly(Ethylene Glycol)-Modified Uricase, Journal of American Society of Nephrology 2001, 12:1001-1009.
Ganson J. et al., Control of Hyperuricemia in Subjects with Refractory Gout, and Induction of antibody Against Poly(ethylene glycol) (PEG), in a Phase I Trial of Subcutaneous Pegylated Urate Oxidase, Arthritis Res Ther 2005, 8(1):R12.
Motojima, K. et al., Cloning and Sequence Analysis of cDNA for Rat Liver Uricase, J. Biol. Chem. 263:16677-16681, American Society for Biochemistry and Molecular Biology (1988).
Sigma Catalog p. 1002, Product Nos. U 3250, 292-8, U3500, U9375, or 03377 (1993).
Kontsek et al., Forty Years of Interferon, 1997, Acta Virologica, vol. 41, pp. 349-352.
European Examination Report for related European Application No. 01 923 265.1 mailed Dec. 13, 2007, European Patent Office, Munich, DE.
Office Action mailed on Sep. 11, 2003; in related U.S. Appl. No. 09/839,946, Williams et al., filed Apr. 19, 2001.
Office Action mailed on Mar. 5, 2004; In related U.S. Appl. No. 09/839,946, Williams et al., filed Apr. 19, 2001.
Office Action mailed on Aug. 2, 2004; In related U.S. Appl. No. 09/839,946, Williams et al., filed Apr. 19, 2001.
Office Action mailed on Jan. 26, 2005; in related U.S. Appl. No. 09/839,946, Williams et al., filed Apr. 19, 2001.
Advisory Action mailed on Dec. 5, 2005; in related U.S. Appl. No. 09/839,946, Williams et al., filed Apr. 19, 2001.
Examiner's Answer to Appeal Brief mailed on Jul. 11, 2006; in related U.S. Appl. No. 09/839,946, Williams et al., filed Apr. 19, 2001.
BPAI Decision decided on Jul. 18, 2007; in related U.S. Appl. No. 09/839,946, Williams et al., filed Apr. 19, 2001.
"Chromatography," Practical Application, ed E. Heftman, part 1, Moscow, "Mir," 1986, pp. 104, 108-109.
Becker MA, et al. N. Engl. J. Med: 2005, 353(23): 2450-2461.
Emmerson BT, N. Engl. J. Med. 1996, 334:445-451.
Forrest A., Hawtoff J., Egorn MJ; Evaluation of a New Program for Population PK/PD Analysis. Applied to Simulated Phase I Data. Clinical Pharmacology and Therapeuticas 49 (2): 153, 1991.
Yamanaka H., et al., Adv. Exp. Med. Biol. 1998, 431:13-18.
Leaustic M. et al., 1983, Rev. Rhum. Osteoartic 50:553-554.
Potaux, L. et al., 1975, Nouv. Presse Med. 4:1109-1112.
Adv. Exp. Med. Biol., 1994, 366:377-387.
Ben-Bassat and Bauer,1987, Nature 326:315.
Otta and Bertini, 1975, Acta Physiol. Latinoam, 25:451-457.
Truscoe, 1967. Enzymologla 33:1 19-32.
Antonopoulos et al., 1961, Blochim. Biophys. Acta 54:213-226.
Embery, 1976, J. Biol. Buccale 4:229-236.
Rinelia et al., 1998, J. Colloid Interface Sci. 197:48-56.
Maccari and Volpi, 2002, Electrophoresis 23:3270-3277.
Scott, 1955, Biochim. Biophys. Acta 18:428-429.
Scott, 1960, Methods Biochem. Anal. 8:145-197.
Laurent et al., 1960, Biochim. Biophys. Acta 42:476-485.
Scott, 1961, Biochem. J. 81:418-424.
Pearce and Mathieson, 1967, Can. J. Biochemistry 45:1565-1576.
Lee, 1973, Fukushima J. Med. Sci. 19:33-39.
Saito, 1955, Kolloid-Z 143:66.
Blumberg and Ogston, 1958, Biochem. J. 68:183-188.
Matsumura et al., 1963, Biochim, Biophys. Acta 69:574-576.
Serafini-Fracassini et al., 1967, Biochem. J. 105:569-575.
Smith et al., 1984, J. Biol. Chem. 259:11046-11051.
Hascall and Heinegard, 1974, J. Biol. Chem. 249:4232-4241, 4242-4249, and 4250-4256.
Heinegard and Hascall, 1974, Arch. Biochem. Biophys. 165:427-441.
Lee et al., 1992, J. Cell Biol. 116: 545-557.
Varelas et al., 1995, Arch. Biochem. Biophys. 321:21-30.
LB Jaques, 1943, Biochern. J. 37:189-195.
AS Jones, 1953, Biochim. Biophys. Acta 10:607-612.
JE Scott, 1955, Chem. and Ind. 168-169.
Cooper JF, 1990, J. Parenter Sci. Technol. 44:13-5.
Kozma et al., 2000, Mol. Cell. Biochem. 203:103-112.
"Designing Custom Peptides," from SIGMA Genosys, pp. 1-2. Accessed Dec. 16, 2004.
A list of GenBank Accession Numbers corresponding to Uricase Family Member Sequences submitted by Applicants to the Examiner in corresponding South Korean Appl. No. 2001-7001569 on Aug. 24, 2004.
A. Ben-Bassat and K. Bauer, "Amino-Terminal Processing of Proteins," Nature vol. 326, Mar. 19, 1987, p. 315.
Abuchowski, A., et al. "Effect of Covalent Attachment of Polyethylene Glycol on Immunogenicity and Cirulating Life of Bovine Liver Catalase." J. Biol. Chem. 252-:3582-3586, American Society for Biochemistry and Molecular Biology (1977).
Berendsen HJC, "A Glimpse of the Holy Grail?" Science, 1998, 282: 642-643.
Bradley et al., "Limits of Cooperativity in a Structurally Modular Protein: Response of the Notch Ankyrin Domain to Analogous Alanine Substitutions in Each Repeat," J. Mol. Biol., 2002, 324: 373-386.
EC Number commentary 1.7.3.3 from the Brenda Enzyme Database at <http://www.brenda-enzymes.info> accessed on Mar. 27, 2008.
Examination Report for Application No. 201002407-3 dated Oct. 22, 2013.
Examination Report for Application No. 2604399 dated Nov. 14, 2013.
Flinta et al., "Sequence Determinants of Cytosolic N-Terminal Protein Processing", Eur J. Biochem 154, pp. 193-196, (1986).
Flinta, Christofer et al., Sequence determinants of cytosolic N-terminal protein processing, Eur. J. Biochem., 1986 Jan 2, 154(1), pp. 193-196.
Forrest A., Hawtoff J., Egorn MJ; Evaluation of a New Program for Population PK/PD Analysis Applied to Simulated Phase I Data. Clinical Pharmacology and Therapeuticas 49 (2): 153, 1991.
Giglione, C et al., "Control of Protein life-span by N-terminal methionine excision", EMBO J. vol. 22 No. 1, pp. 13-23, 2003.
Hershfield, M.S.. "Biochemistry and Immonology of Poly(ethylene glycol)-Modified Adenosine Deaminase (PEG-ADA)," In: ACS Symposium Series 680. Poly(elhylene glycol). Chemistry and Biological Applications, Harris, J.M. and Zalipsky, S., eds.,American Chemical Society. Washington, DC. pp. 145-154 (1997).
Hirel et al., Extent of N-terminal methionine excision from *Escherichia coli* proteins is governed by the side-chain length of the penultimate amino acid, (1989) Proc. Natl. Acad. Sci. U.S.A. 86(21): 8247-8251.
International Preliminary Report on Patentability for International Application No. PCT US06 13502 dated Jul. 16, 2007.
International Search Report for International Application No. PCT US2006 013502, dated Dec. 13, 2006.
International Search Report for International Application No. PCT US2006 013502 dated Dec. 13, 2006.
International Search Report for International Application No. PCTUS0140069 dated Dec. 12, 2001.
International Search Report for International Application No. PCTUS9917514 dated Mar. 17, 2000.
International Search Report for International Application No. PCTUS9917678 dated Feb 2. 2000.

(56) References Cited

OTHER PUBLICATIONS

Li et al., Mutations at the S1 Sites of methionine Aminopeptidases from *Escherichia coli* and *Homo sapiens* Reveal the residues Critical for Substrate Specificity, (May 14, 2004), J. Biol. Chem. 279(20): 21128-21134.

Moerschell et al., The Specificities of Yeast Methionine Aminopeptidase and Acetylation of Amino-terminal Methionine in Vivo, (1990) J. Biol. Chem. 265: 19638-19643.

Ngo et al., "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

Office Action mailed on Jul. 20, 2005; in related U.S. Appl. No. 09/839,946, Williams et al., filed Apr. 19, 2001.

Rudinger J, "Characteristics of the amino acids as components of a peptide hormone sequence," Peptide Hormones, JA Parsons Edition, University Park Press, Jun. 1976, pp. 1-7.

Schinzel R et al., "The phosphate recognition site of *Escherichia coli* maltodextrin phosphorylase," FEBS, Jul. 1991, 286(1,2): 125-128.

Sherman et al., "Methionine or not methionine at the beginning of a protein", BioEssays, vol. 3, Issue 1, pp. 27-31, Jul. 1985.

Voet et al., Biochemistry, Second Edition, John Wiley & Sons, Inc., 1995, pp. 235-241.

\* cited by examiner

```
  1        ATG--------------ACTTACAAAAAGAATGATGAGGTAGAGTTTGTCCGAACTGGC
  1        M  -  -  -  -  -  T  Y  K  K  N  D  E  V  E  F  V  R  T  G

61        TATGGGAAGGATATGATAAAAGTTCTCCATATTCAGCGAGATGGAAAATATCACAGCATT
 21         Y  G  K  D  M  I  K  V  L  H  I  Q  R  D  G  K  Y  H  S  I

121        AAAGAGGTGGCAACTACAGTGCAACTGACTTTGAGCTCCAAAAAAGATTACCTGCATGGA
 41         K  E  V  A  T  T  V  Q  L  T  L  S  S  K  K  D  Y  L  H  G

181        GACAATTCAGATGTCATCCCTACAGACACCATCAAGAACACAGTTAATGTCCTGGCGAAG
 61         D  N  S  D  V  I  P  T  D  T  I  K  N  T  V  N  V  L  A  K

241        TTCAAAGGCATCAAAAGCATAGAAACTTTTGCTGTGACTATCTGTGAGCATTTCCTTTCT
 81         F  K  G  I  K  S  I  E  T  F  A  V  T  I  C  E  H  F  L  S

301        TCCTTCAAGCATGTCATCAGAGCTCAAGTCTATGTGGAAGAAGTTCCTTGGAAGCGTTTT
101         S  F  K  H  V  I  R  A  Q  V  Y  V  E  E  V  P  W  K  R  F

361        GAAAAGAATGGAGTTAAGCATGTCCATGCATTTATTTATACTCCTACTGGAACGCACTTC
121         E  K  N  G  V  K  H  V  H  A  F  I  Y  T  P  T  G  T  H  F

421        TGTGAGGTTGAACAGATAAGGAATGGACCTCCAGTCATTCATTCTGGAATCAAAGACCTA
141         C  E  V  E  Q  I  R  N  G  P  P  V  I  H  S  G  I  K  D  L

481        AAAGTCTTGAAAACAACCCAGTCTGGCTTTGAAGGATTCATCAAGGACCAGTTCACCACC
161         K  V  L  K  T  T  Q  S  G  F  E  G  F  I  K  D  Q  F  T  T

541        CTCCCTGAGGTGAAGGACCGGTGCTTTGCCACCCAAGTGTACTGCAAATGGCGCTACCAC
181         L  P  E  V  K  D  R  C  F  A  T  Q  V  Y  C  K  W  R  Y  H

601        CAGGGCAGAGATGTGGACTTTGAGGCCACCTGGGACACTGTTAGGAGCATTGTCCTGCAG
201         Q  G  R  D  V  D  F  E  A  T  W  D  T  V  R  S  I  V  L  Q
                          ApaI
                            |
661        AAATTTGCTGGGCCCTATGACAAAGGCGAGTACTCGCCCTCTGTCCAGAAGACACTCTAT
221         K  F  A  G  P  Y  D  K  G  E  Y  S  P  S  V  Q  K  T  L  Y

721        GACATCCAGGTGCTCACCCTGGGCCAGGTTCCTGAGATAGAAGATATGGAAATCAGCCTG
241         D  I  Q  V  L  T  L  G  Q  V  P  E  I  E  D  M  E  I  S  L

781        CCAAATATTCACTACTTAAACATAGACATGTCCAAAATGGGACTGATCAACAAGGAAGAG
261         P  N  I  H  Y  L  N  I  D  M  S  K  M  G  L  I  N  K  E  E
                                NdeI
                                  |
841        GTCTTGCTACCTTTAGACAATCCATATGGAAAAATTACTGGTACAGTCAAGAGGAAGTTG
281         V  L  L  P  L  D  N  P  Y  G  K  I  T  G  T  V  K  R  K  L
                                EcoRI                      SpeI BamHI
                                  |                          |    |
901        TCTTCAAGACTGTGAaagccgaattccagcacactggcggccgttactagtggatcc
301         S  S  R  L  *
```

Figure 2.

```
                        20                  40                  60
Pig         MAHYRNDYKKNDEVEFVRTGYGKDMIKVLHIQRDGKYHSIKEVATSVQLTLSSKKDYLHG
PBC-ΔNC     M-----TYKKNDEVEFVRTGYGKDMIKVLHIQRDGKYHSIKEVATTVQLTLSSKKDYLHG
Pig-KS-ΔN   M-----TYKKNDEVEFVRTGYGKDMIKVLHIQRDGKYHSIKEVATTVQLTLSSKKDYLHG
                  *                                       *
                        80                  100                 120
Pig         DNSDVIPTDTIKNTVNVLAKFKGIKSIETFAVTICEHFLSSFKHVIRAQVYVEEVPWKRF
PBC-ΔNC     DNSDVIPTDTIKNTVNVLAKFKGIKSIETFAVTICEHFLSSFKHVIRAQVYVEEVPWKRF
Pig-KS-ΔN   DNSDVIPTDTIKNTVNVLAKFKGIKSIETFAVTICEHFLSSFKHVIRAQVYVEEVPWKRF 140                 160                 180
Pig         EKNGVKHVHAFIYTPTGTHFCEVEQIRNGPPVIHSGIKDLKVLKTTQSGFEGFIKDQFTT
PBC-ΔNC     EKNGVKHVHAFIYTPTGTHFCEVEQIRNGPPVIHSGIKDLKVLKTTQSGFEGFIKDQFTT
Pig-KS-ΔN   EKNGVKHVHAFIYTPTGTHFCEVEQIRNGPPVIHSGIKDLKVLKTTQSGFEGFIKDQFTT 200                 220                 240
Pig         LPEVKDRCFATQVYCKWRYHQGRDVDFEATWDTVRSIVLQKFAGPYDKGEYSPSVQKTLY
PBC-ΔNC     LPEVKDRCFATQVYCKWRYHQGRDVDFEATWDTVRSIVLQKFAGPYDKGEYSPSVQKTLY
Pig-KS-ΔN   LPEVKDRCFATQVYCKWRYHQGRDVDFEATWDTVRSIVLQKFAGPYDKGEYSPSVQKTLY 260                 280                 300
Pig         DIQVLTLGQVPEIEDMEISLPNIHYLNIDMSKMGLINKEEVLLPLDNPYGRITGTVKRKL
PBC-ΔNC     DIQVLSLSRVPEIEDMEISLPNIHYFNIDMSKMGLINKEEVLLPLDNPYGKITGTVKRKL
Pig-KS-ΔN   DIQVLTLGQVPEIEDMEISLPNIHYLNIDMSKMGLINKEEVLLPLDNPYGKITGTVKRKL
                 o oo                o                         *

Pig         TSRL
PBC-ΔNC     S---
Pig-KS-ΔN   SSRL
            *
```

Figure 3.

SEQUENCE LISTING

```
<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      Pig Liver Uricase (sense) oligonucleotide

<400> SEQUENCE: 1
gcgcgaattc catggctcat taccgtaatg actaca                              36

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      Pig Liver Uricase (antisense) oligonucleotide

<400> SEQUENCE: 2
gcgctctaga agcttccatg gtcacagcct tgaagtcagc                          40

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      Baboon (D3H) Liver Uricase (sense) oligonucleotide
```

<400> SEQUENCE: 3
gcgcgaattc catggcccac taccataaca actat                35

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      Baboon (D3H) Liver Uricase (antisense) oligonucleotide

<400> SEQUENCE: 4
gcgcccatgg tctagatcac agtcttgaag acaacttcct           40

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      PBC-DeltaNC Uricase (sense) oligonucleotide

<400> SEQUENCE: 5
gcgcatatga cttacaaaaa gaatgatgag gtagag               36

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: Synthetic
      PBC-DeltaNC Uricase (antisense) oligonucleotide

<400> SEQUENCE: 6
ccgtctagat taagacaact tcctcttgac tgtaccagta atttttccgt atgg    54

<210> SEQ ID NO 7
<211> LENGTH: 299
<212> TYPE: PRT
<213> ORGANISM: Artificial Sequence
<220> FEATURE:
<223> OTHER INFORMATION: Description of Artificial Sequence: Synthetic
      Pig-KS-DeltaN polypeptide

<400> SEQUENCE: 7

Met Thr Tyr Lys Lys Asn Asp Glu Val Glu Phe Val Arg Thr Gly Tyr
1               5                   10                  15

Gly Lys Asp Met Ile Lys Val Leu His Ile Gln Arg Asp Gly Lys Tyr
            20                  25                  30

His Ser Ile Lys Glu Val Ala Thr Thr Val Gln Leu Thr Leu Ser Ser
        35                  40                  45

Lys Lys Asp Tyr Leu His Gly Asp Asn Ser Asp Val Ile Pro Thr Asp
    50                  55                  60

Thr Ile Lys Asn Thr Val Asn Val Leu Ala Lys Phe Lys Gly Ile Lys
65                  70                  75                  80

Ser Ile Glu Thr Phe Ala Val Thr Ile Cys Glu His Phe Leu Ser Ser
                85                  90                  95

Phe Lys His Val Ile Arg Ala Gln Val Tyr Val Glu Glu Val Pro Trp
            100                 105                 110

Lys Arg Phe Glu Lys Asn Gly Val Lys His Val His Ala Phe Ile Tyr
            115                 120                 125

```
Thr Pro Thr Gly Thr His Phe Cys Glu Val Glu Gln Ile Arg Asn Gly
    130                 135                 140

Pro Pro Val Ile His Ser Gly Ile Lys Asp Leu Lys Val Leu Lys Thr
145                 150                 155                 160

Thr Gln Ser Gly Phe Glu Gly Phe Ile Lys Asp Gln Phe Thr Thr Leu
                    165                 170                 175

Pro Glu Val Lys Asp Arg Cys Phe Ala Thr Gln Val Tyr Cys Lys Trp
                180                 185                 190

Arg Tyr His Gln Gly Arg Asp Val Asp Phe Glu Ala Thr Trp Asp Thr
            195                 200                 205

Val Arg Ser Ile Val Leu Gln Lys Phe Ala Gly Pro Tyr Asp Lys Gly
210                 215                 220

Glu Tyr Ser Pro Ser Val Gln Lys Thr Leu Tyr Asp Ile Gln Val Leu
225                 230                 235                 240

Thr Leu Gly Gln Val Pro Glu Ile Glu Asp Met Glu Ile Ser Leu Pro
                245                 250                 255

Asn Ile His Tyr Leu Asn Ile Asp Met Ser Lys Met Gly Leu Ile Asn
            260                 265                 270

Lys Glu Glu Val Leu Leu Pro Leu Asp Asn Pro Tyr Gly Lys Ile Thr
        275                 280                 285

Gly Thr Val Lys Arg Lys Leu Ser Ser Arg Leu
290                 295

<210> SEQ ID NO 8
<211> LENGTH: 298
<212> TYPE: PRT
<213> ORGANISM: Artificial Sequence
<220> FEATURE:
<223> OTHER INFORMATION: Description of Artificial Sequence: Synthetic
      Pig-KS-DeltaN without starting Met polypeptide

<400> SEQUENCE: 8

Thr Tyr Lys Lys Asn Asp Glu Val Glu Phe Val Arg Thr Gly Tyr Gly
1               5                   10                  15

Lys Asp Met Ile Lys Val Leu His Ile Gln Arg Asp Gly Lys Tyr His
                20                  25                  30

Ser Ile Lys Glu Val Ala Thr Thr Val Gln Leu Thr Leu Ser Ser Lys
            35                  40                  45

Lys Asp Tyr Leu His Gly Asp Asn Ser Asp Val Ile Pro Thr Asp Thr
        50                  55                  60

Ile Lys Asn Thr Val Asn Val Leu Ala Lys Phe Lys Gly Ile Lys Ser
65                  70                  75                  80

Ile Glu Thr Phe Ala Val Thr Ile Cys Glu His Phe Leu Ser Ser Phe
                85                  90                  95

Lys His Val Ile Arg Ala Gln Val Tyr Val Glu Val Pro Trp Lys
            100                 105                 110

Arg Phe Glu Lys Asn Gly Val Lys His Val His Ala Phe Ile Tyr Thr
        115                 120                 125

Pro Thr Gly Thr His Phe Cys Glu Val Glu Gln Ile Arg Asn Gly Pro
    130                 135                 140

Pro Val Ile His Ser Gly Ile Lys Asp Leu Lys Val Leu Lys Thr Thr
145                 150                 155                 160

Gln Ser Gly Phe Glu Gly Phe Ile Lys Asp Gln Phe Thr Thr Leu Pro
                165                 170                 175

Glu Val Lys Asp Arg Cys Phe Ala Thr Gln Val Tyr Cys Lys Trp Arg
            180                 185                 190
```

Tyr His Gln Gly Arg Asp Val Asp Phe Glu Ala Thr Trp Asp Thr Val
            195                 200                 205

Arg Ser Ile Val Leu Gln Lys Phe Ala Gly Pro Tyr Asp Lys Gly Glu
    210                 215                 220

Tyr Ser Pro Ser Val Gln Lys Thr Leu Tyr Asp Ile Gln Val Leu Thr
225                 230                 235                 240

Leu Gly Gln Val Pro Glu Ile Glu Asp Met Glu Ile Ser Leu Pro Asn
                245                 250                 255

Ile His Tyr Leu Asn Ile Asp Met Ser Lys Met Gly Leu Ile Asn Lys
            260                 265                 270

Glu Glu Val Leu Leu Pro Leu Asp Asn Pro Tyr Gly Lys Ile Thr Gly
                275                 280                 285

Thr Val Lys Arg Lys Leu Ser Ser Arg Leu
            290                 295

<210> SEQ ID NO 9
<211> LENGTH: 897
<212> TYPE: DNA
<213> ORGANISM: Artificial Sequence
<220> FEATURE:
<223> OTHER INFORMATION: Description of Artificial Sequence: Synthetic
      Pig-KS-DeltaNA polynucleotide

<400> SEQUENCE: 9
atgacttaca aaagaatga tgaggtagag tttgtccgaa ctggctatgg gaaggatatg      60
ataaaagttc tccatattca gcgagatgga aaatatcaca gcattaaaga ggtggcaact     120
acagtgcaac tgactttgag ctccaaaaaa gattacctgc atggagacaa ttcagatgtc     180
atccctacag acaccatcaa gaacacagtt aatgtcctgg cgaagttcaa aggcatcaaa     240
agcatagaaa cttttgctgt gactatctgt gagcatttcc tttcttcctt caagcatgtc     300
atcagagctc aagtctatgt ggaagaagtt ccttggaagc gttttgaaaa gaatggagtt     360
aagcatgtcc atgcatttat ttatactcct actggaacgc acttctgtga ggttgaacag     420
ataaggaatg gacctccagt cattcattct ggaatcaaag acctaaaagt cttgaaaaca     480
acccagtctg gctttgaagg attcatcaag gaccagttca ccaccctccc tgaggtgaag     540
gaccggtgct tgccaccca agtgtactgc aaatggcgct accaccaggg cagagatgtg     600
gactttgagg ccacctggga cactgttagg agcattgtcc tgcagaaatt tgctgggccc     660
tatgacaaag gcgagtactc gccctctgtc cagaagacac tctatgacat ccaggtgctc     720
accctgggcc aggttcctga gatagaagat atggaaatca gcctgccaaa tattcactac     780
ttaaacatag acatgtccaa aatgggactg atcaacaagg aagaggtctt gctacctta      840 gacaatccat atggaaaaat tactggtaca gtcaagagga gttgtcttc aagactg        897

<210> SEQ ID NO 10
<211> LENGTH: 894
<212> TYPE: DNA
<213> ORGANISM: Artificial Sequence
<220> FEATURE:
<223> OTHER INFORMATION: Description of Artificial Sequence: Synthetic
      Pig-KS-DeltaN without starting ATG polynucleotide

<400> SEQUENCE: 10
acttacaaaa agaatgatga ggtagagttt gtccgaactg gctatgggaa ggatatgata     60
aaagttctcc atattcagcg agatggaaaa tatcacagca ttaaagaggt ggcaactaca     120
gtgcaactga ctttgagctc caaaaagat tacctgcatg gagacaattc agatgtcatc     180

```
cctacagaca ccatcaagaa cacagttaat gtcctggcga agttcaaagg catcaaaagc    240
atagaaactt tgctgtgac tatctgtgag catttccttt cttccttcaa gcatgtcatc    300
agagctcaag tctatgtgga agaagttcct tggaagcgtt tgaaaagaa tggagttaag    360 catgtccatg catttattta tactcctact ggaacgcact tctgtgaggt tgaacagata    420
aggaatggac ctccagtcat tcattctgga atcaaagacc taaaagtctt gaaacaacc    480 cagtctggct ttgaaggatt catcaaggac cagttcacca ccctccctga ggtgaaggac    540
cggtgctttg ccacccaagt gtactgcaaa tggcgctacc accagggcag agatgtggac    600
tttgaggcca cctgggacac tgttaggagc attgtcctgc agaaatttgc tgggccctat    660
gacaaaggcg agtactcgcc ctctgtccag aagacactct atgacatcca ggtgctcacc    720
ctgggccagg ttcctgagat agaagatatg gaaatcagcc tgccaaatat tcactactta    780
aacatagaca tgtccaaaat gggactgatc aacaaggaag aggtcttgct acctttagac    840
aatccatatg gaaaaattac tggtacagtc aagaggaagt tgtcttcaag actg          894
```

<210> SEQ ID NO 11
<211> LENGTH: 304
<212> TYPE: PRT
<213> ORGANISM: Sus scrofa

<400> SEQUENCE: 11

```
Met Ala His Tyr Arg Asn Asp Tyr Lys Lys Asn Asp Glu Val Glu Phe
1               5                   10                  15

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
```

```
                245                 250                 255
Glu Ile Ser Leu Pro Asn Ile His Tyr Leu Asn Ile Asp Met Ser Lys
            260                 265                 270

Met Gly Leu Ile Asn Lys Glu Val Leu Leu Pro Leu Asp Asn Pro
        275                 280                 285

Tyr Gly Arg Ile Thr Gly Thr Val Lys Lys Leu Thr Ser Arg Leu
    290                 295                 300

<210> SEQ ID NO 12
<211> LENGTH: 296
<212> TYPE: PRT
<213> ORGANISM: Artificial Sequence
<220> FEATURE:
<223> OTHER INFORMATION: Description of Artificial Sequence: Synthetic
      PBC-DeltaNC polypeptide

<400> SEQUENCE: 12

Met Thr Tyr Lys Lys Asn Asp Glu Val Glu Phe Val Arg Thr Gly Tyr
1               5                   10                  15

Gly Lys Asp Met Ile Lys Val Leu His Ile Gln Arg Asp Gly Lys Tyr
            20                  25                  30

His Ser Ile Lys Glu Val Ala Thr Thr Val Gln Leu Thr Leu Ser Ser
        35                  40                  45

Lys Lys Asp Tyr Leu His Gly Asp Asn Ser Asp Val Ile Pro Thr Asp
    50                  55                  60

Thr Ile Lys Asn Thr Val Asn Val Leu Ala Lys Phe Lys Gly Ile Lys
65                  70                  75                  80

Ser Ile Glu Thr Phe Ala Val Thr Ile Cys His Phe Leu Ser Ser
                85                  90                  95

Phe Lys His Val Ile Arg Ala Gln Val Tyr Val Glu Glu Val Pro Trp
            100                 105                 110

Lys Arg Phe Glu Lys Asn Gly Val Lys His Val His Ala Phe Ile Tyr
        115                 120                 125

Thr Pro Thr Gly Thr His Phe Cys Glu Val Glu Gln Ile Arg Asn Gly
    130                 135                 140

Pro Pro Val Ile His Ser Gly Ile Lys Asp Leu Lys Val Leu Lys Thr
145                 150                 155                 160

Thr Gln Ser Gly Phe Glu Gly Phe Ile Lys Asp Gln Phe Thr Thr Leu
                165                 170                 175

Pro Glu Val Lys Asp Arg Cys Phe Ala Thr Gln Val Tyr Cys Lys Trp
            180                 185                 190

Arg Tyr His Gln Gly Arg Asp Val Asp Phe Glu Ala Thr Trp Asp Thr
        195                 200                 205

Val Arg Ser Ile Val Leu Gln Lys Phe Ala Gly Pro Tyr Asp Lys Gly
    210                 215                 220

Glu Tyr Ser Pro Ser Val Gln Lys Thr Leu Tyr Asp Ile Gln Val Leu
225                 230                 235                 240

Ser Leu Ser Arg Val Pro Glu Ile Glu Asp Met Glu Ile Ser Leu Pro
                245                 250                 255

Asn Ile His Tyr Phe Asn Ile Asp Met Ser Lys Met Gly Leu Ile Asn
            260                 265                 270

Lys Glu Glu Val Leu Leu Pro Leu Asp Asn Pro Tyr Gly Lys Ile Thr
        275                 280                 285

Gly Thr Val Lys Arg Lys Leu Ser
    290                 295
```

-continued

<210> SEQ ID NO 13
<211> LENGTH: 295
<212> TYPE: PRT
<213> ORGANISM: Artificial Sequence
<220> FEATURE:
<223> OTHER INFORMATION: Description of Artificial Sequence: Synthetic
      PBC-DeltaNC without starting Met polypeptide

<400> SEQUENCE: 13

Thr Tyr Lys Lys Asn Asp Glu Val Glu Phe Val Arg Thr Gly Tyr Gly
 1               5                  10                  15

Lys Asp Met Ile Lys Val Leu His Ile Gln Arg Asp Gly Lys Tyr His
            20                  25                  30

Ser Ile Lys Glu Val Ala Thr Thr Val Gln Leu Thr Leu Ser Ser Lys
        35                  40                  45

Lys Asp Tyr Leu His Gly Asp Asn Ser Asp Val Ile Pro Thr Asp Thr
    50                  55                  60

Ile Lys Asn Thr Val Asn Val Leu Ala Lys Phe Lys Gly Ile Lys Ser
65                  70                  75                  80

Ile Glu Thr Phe Ala Val Thr Ile Cys Glu His Phe Leu Ser Ser Phe
                85                  90                  95

Lys His Val Ile Arg Ala Gln Val Tyr Val Glu Val Pro Trp Lys
            100                 105                 110

Arg Phe Glu Lys Asn Gly Val Lys His Val His Ala Phe Ile Tyr Thr
        115                 120                 125

Pro Thr Gly Thr His Phe Cys Glu Val Glu Gln Ile Arg Asn Gly Pro
    130                 135                 140

Pro Val Ile His Ser Gly Ile Lys Asp Leu Lys Val Leu Lys Thr Thr
145                 150                 155                 160

Gln Ser Gly Phe Glu Gly Phe Ile Lys Asp Gln Phe Thr Thr Leu Pro
                165                 170                 175

Glu Val Lys Asp Arg Cys Phe Ala Thr Gln Val Tyr Cys Lys Trp Arg
            180                 185                 190

Tyr His Gln Gly Arg Asp Val Asp Phe Glu Ala Thr Trp Asp Thr Val
        195                 200                 205

Arg Ser Ile Val Leu Gln Lys Phe Ala Gly Pro Tyr Asp Lys Gly Glu
    210                 215                 220

Tyr Ser Pro Ser Val Gln Lys Thr Leu Tyr Asp Ile Gln Val Leu Ser
225                 230                 235                 240

Leu Ser Arg Val Pro Glu Ile Glu Asp Met Glu Ile Ser Leu Pro Asn
                245                 250                 255

Ile His Tyr Phe Asn Ile Asp Met Ser Lys Met Gly Leu Ile Asn Lys
            260                 265                 270

Glu Glu Val Leu Leu Pro Leu Asp Asn Pro Tyr Gly Lys Ile Thr Gly
        275                 280                 285

Thr Val Lys Arg Lys Leu Ser
    290                 295

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      PBC-DeltaNC (Fragment 44-56 of PBC-DeltaNC) peptide

<400> SEQUENCE: 14

Ala Thr Thr Val Gln Leu Thr Leu Ser Ser Lys Lys Asp
1               5                   10

<210> SEQ ID NO 15
<211> LENGTH: 936
<212> TYPE: DNA
<213> ORGANISM: Papio hamadryas

<400> SEQUENCE: 15

| | | | | | |
|---|---|---|---|---|---|
| ccagaagaaa | atggccgact | accataacaa | ctataaaaag | aatgatgaat | tggagtttgt | 60 |
| ccgaactggc | tatgggaagg | atatggtaaa | agttctccat | attcagcgag | atggaaaata | 120 |
| tcacagcatt | aaagaggtgg | caacttcagt | gcaacttact | ctgagttcca | aaaaagatta | 180 |
| cctgcatgga | gataattcag | atatcatccc | tacagacacc | atcaagaaca | cagttcatgt | 240 |
| cttggcaaag | tttaagggaa | tcaaaagcat | agaagccttt | ggtgtgaata | tttgtgagta | 300 |
| ttttcttct | tcttttaacc | atgtaatccg | agctcaagtc | tacgtggaag | aaatcccttg | 360 |
| gaagcgtctt | gaaaagaatg | gagttaagca | tgtccatgca | tttattcaca | ctcccactgg | 420 |
| aacacacttc | tgtgaagttg | aacaactgag | aagtggaccc | ccgtcatta | cttctggaat | 480 |
| caaagacctc | aaggtcttga | aaacaacaca | gtctggattt | gaaggtttca | tcaaggacca | 540 |
| gttcaccacc | ctccctgagg | tgaaggaccg | atgctttgcc | acccaagtgt | actgcaagtg | 600 |
| gcgctaccac | cagtgcaggg | atgtggactt | cgaggctacc | tggggcacca | ttcgggacct | 660 |
| tgtcctggag | aaatttgctg | ggccctatga | caaaggcgag | tactcaccct | ctgtgcagaa | 720 |
| gaccctctat | gatatccagg | tgctctccct | gagccgagtt | cctgagatag | aagatatgga | 780 |
| aatcagcctg | ccaaacattc | actacttcaa | tatagacatg | tccaaaatgg | gtctgatcaa | 840 |
| caaggaagag | gtcttgctgc | cattagacaa | tccatatgga | aaaattactg | gtacagtcaa | 900 |
| gaggaagttg | tcttcaagac | tgtgacattg | tggcca | | | 936 |

<210> SEQ ID NO 16
<211> LENGTH: 304
<212> TYPE: PRT
<213> ORGANISM: Papio hamadryas

<400> SEQUENCE: 16

Met Ala Asp Tyr His Asn Asn Tyr Lys Lys Asn Asp Glu Leu Glu Phe
1               5                   10                  15

Val Arg Thr Gly Tyr Gly Lys Asp Met Val Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
        50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Gly Val Asn Ile Cys Glu
                85                  90                  95

Tyr Phe Leu Ser Ser Phe Asn His Val Ile Arg Ala Gln Val Tyr Val
            100                 105                 110

Glu Glu Ile Pro Trp Lys Arg Leu Glu Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Pro Val Ile Thr Ser Gly Ile Lys Asp Leu

```
                145                 150                 155                 160
Lys Val Leu Lys Thr Thr Gln Ser Gly Phe Glu Gly Phe Ile Lys Asp
                    165                 170                 175

Gln Phe Thr Thr Leu Pro Glu Val Lys Asp Arg Cys Phe Ala Thr Gln
                180                 185                 190

Val Tyr Cys Lys Trp Arg Tyr His Gln Cys Arg Asp Val Asp Phe Glu
            195                 200                 205

Ala Thr Trp Gly Thr Ile Arg Asp Leu Val Leu Glu Lys Phe Ala Gly
            210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
                260                 265                 270

Met Gly Leu Ile Asn Lys Glu Glu Val Leu Leu Pro Leu Asp Asn Pro
            275                 280                 285

Tyr Gly Lys Ile Thr Gly Thr Val Lys Arg Lys Leu Ser Ser Arg Leu
290                 295                 300
```

VARIANT FORMS OF URATE OXIDASE AND USE THEREOF

CROSS REFERENCE TO RELATED APPLICATIONS

The present application is a continuation of U.S. application Ser. No. 13/461,170 filed May 1, 2012, now allowed, which is a divisional application of U.S. application Ser. No. 11/918,297 filed Dec. 11, 2008, now U.S. Pat. No. 8,188,224, which is a national stage filing of corresponding international application number PCT/US2006/013660, filed on Apr. 11, 2006, which claims priority to and benefit of U.S. provisional application Ser. No. 60/670,573, filed on Apr. 11, 2005, the disclosure of which is being incorporated by reference herein.

FIELD OF INVENTION

The present invention relates to genetically modified proteins with uricolytic activity. More specifically, the invention relates to proteins comprising truncated urate oxidases and methods for producing them.

BACKGROUND OF THE INVENTION

The terms urate oxidase and uricase are used herein interchangeably. Urate oxidases (uricases; E.C. 1.7.3.3) are enzymes which catalyze the oxidation of uric acid to a more soluble product, allantoin, a purine metabolite that is more readily excreted. Humans do not produce enzymatically active uricase, as a result of several mutations in the gene for uricase acquired during the evolution of higher primates. Wu, X, et al., (1992) *J Mol Evol* 34:78-84, incorporated herein by reference in its entirety. As a consequence, in susceptible individuals, excessive concentrations of uric acid in the blood (hyperuricemia) can lead to painful arthritis (gout), disfiguring urate deposits (tophi) and renal failure. In some affected individuals, available drugs such as allopurinol (an inhibitor of uric acid synthesis) produce treatment-limiting adverse effects or do not relieve these conditions adequately. Hande, K R, et al., (1984) *Am J Med* 76:47-56; Fam, A G, (1990) *Bailliere's Clin Rheumatol* 4:177-192, each incorporated herein by reference in its entirety. Injections of uricase can decrease hyperuricemia and hyperuricosuria, at least transiently. Since uricase is a foreign protein in humans, even the first injection of the unmodified protein from *Aspergillus flavus* has induced anaphylactic reactions in several percent of treated patients (Pui, C-H, et al., (1997) *Leukemia* 11:1813-1816, incorporated herein by reference in its entirety), and immunologic responses limit its utility for chronic or intermittent treatment. Donadio, D, et al., (1981) *Nouv Presse Med* 10:711-712; Leaustic, M, et al., (1983) *Rev Rhum Mal Osteoartic* 50:553-554, each incorporated herein by reference in its entirety.

The sub-optimal performance of available treatments for hyperuricemia has been recognized for several decades. Kissel, P, et al., (1968) *Nature* 217:72-74, incorporated herein by reference in its entirety. Similarly, the possibility that certain groups of patients with severe gout might benefit from a safe and effective form of injectable uricase has been recognized for many years. Davis, F F, et al., (1978) in G B Broun, et al., (Eds.) *Enzyme Engineering, Vol.* 4 (pp. 169-173) New York, Plenum Press; Nishimura, H, et al., (1979) *Enzyme* 24:261-264; Nishimura, H, et al., (1981) *Enzyme* 26:49-53; Davis, S, et al., (1981) *Lancet* 2(8241):281-283; Abuchowski, A, et al., (1981) *J Pharmacol Exp Ther* 219:352-354; Chen, R H-L, et al., (1981) *Biochim Biophys Acta* 660:293-298; Chua, C C, et al., (1988) *Ann Int Med* 109:114-117; Greenberg, M L, et al., (1989) *Anal Biochem* 176:290-293, each incorporated herein by reference in its entirety. Uricases derived from animal organs are nearly insoluble in solvents that are compatible with safe administration by injection. U.S. Pat. No. 3,616,231, incorporated herein by reference in its entirety. Certain uricases derived from plants or from microorganisms are more soluble in medically acceptable solvents. However, injection of the microbial enzymes quickly induces immunological responses that can lead to life-threatening allergic reactions or to inactivation and/or accelerated clearance of the uricase from the circulation. Donadio, et al., (1981); Leaustic, et al., (1983). Enzymes based on the deduced amino acid sequences of uricases from mammals, including pig and baboon, or from insects, such as, for example, *Drosophila melanogaster* or *Drosophila pseudoobscura* (Wallrath, L L, et al., (1990) *Mol Cell Biol* 10:5114-5127, incorporated herein by reference in its entirety), have not been suitable candidates for clinical use, due to problems of immunogenicity and insolubility at physiological pH.

Previously, investigators have used injected uricase to catalyze the conversion of uric acid to allantoin in vivo. See Pui, et al., (1997). This is the basis for the use in France and Italy of uricase from the fungus *Aspergillus flavus* (URICOZYME®) to prevent or temporarily correct the hyperuricemia associated with cytotoxic therapy for hematologic malignancies and to transiently reduce severe hyperuricemia in patients with gout. Potaux, L, et al., (1975) *Nouv Presse Med* 4:1109-1112; Legoux, R, et al., (1992) *J Biol Chem* 267: 8565-8570; U.S. Pat. Nos. 5,382,518 and 5,541,098, each incorporated herein by reference in its entirety. Because of its short circulating lifetime, URICOZYME® requires daily injections. Furthermore, it is not well suited for long-term therapy because of its immunogenicity.

Certain uricases are useful for preparing conjugates with poly(ethylene glycol) or poly(ethylene oxide) (both referred to as PEG) to produce therapeutically efficacious forms of uricase having increased protein half-life and reduced immunogenicity. U.S. Pat. Nos. 4,179,337, 4,766,106, 4,847,325, and 6,576,235; U.S. Patent Application Publication US2003/0082786A1, each incorporated herein by reference in its entirety. Conjugates of uricase with polymers other than PEG have also been described. U.S. Pat. No. 4,460,683, incorporated herein by reference in its entirety.

In nearly all of the reported attempts to PEGylate uricase (i.e. to covalently couple PEG to uricase), the PEG is attached primarily to amino groups, including the amino-terminal residue and the available lysine residues. In the uricases commonly used, the total number of lysines in each of the four identical subunits is between 25 (*Aspergillus flavus* (U.S. Pat. No. 5,382,518, incorporated herein by reference in its entirety)) and 29 (pig (Wu, X, et al., (1989) Proc Natl Acad Sci USA 86:9412-9416, incorporated herein by reference in its entirety)). Some of the lysines are unavailable for PEGylation in the native conformation of the enzyme. The most common approach to reducing the immunogenicity of uricase has been to couple large numbers of strands of low molecular weight PEG. This has invariably resulted in large decreases in the enzymatic activity of the resultant conjugates.

A single intravenous injection of a preparation of *Candida utilis* uricase coupled to 5 kDa PEG reduced serum urate to undetectable levels in five human subjects whose average pre-injection serum urate concentration is 6.2 mg/dl, which is within the normal range. Davis, et al., (1981). The subjects were given an additional injection four weeks later, but their responses were not reported. No antibodies to uricase were detected following the second (and last) injection, using a relatively insensitive gel diffusion assay. This reference reported no results from chronic or subchronic treatments of human patients or experimental animals.

A preparation of uricase from *Arthrobacter protoformiae* coupled to 5 kDa PEG was used to temporarily control hyperuricemia in a single patient with lymphoma whose pre-injection serum urate concentration is 15 mg/dL. Chua, et al., (1988). Because of the critical condition of the patient and the short duration of treatment (four injections during 14 days), it is not possible to evaluate the long-term efficacy or safety of the conjugate.

Improved protection from immune recognition is enabled by modifying each uricase subunit with 2-10 strands of high molecular weight PEG (>5 kD-120 kD) Saifer, et al. (U.S. Pat. No. 6,576,235; (1994) Adv Exp Med Biol 366:377-387, each incorporated herein by reference in its entirety). This strategy enabled retention of >75% enzymatic activity of uricase from various species, following PEGylation, enhanced the circulating life of uricase, and enabled repeated injection of the enzyme without eliciting antibodies in mice and rabbits.

Hershfield and Kelly (International Patent Publication WO 00/08196; U.S. Application No. 60/095,489, incorporated herein by reference in its entirety) developed means for providing recombinant uricase proteins of mammalian species with optimal numbers of PEGylation sites. They used PCR techniques to increase the number of available lysine residues at selected points on the enzyme which is designed to enable reduced recognition by the immune system, after subsequent PEGylation, while substantially retaining the enzyme's uricolytic activity. Some of their uricase proteins are truncated at the carboxy and/or amino termini. They do not provide for directing other specific genetically-induced alterations in the protein.

In this application, the term "immunogenicity" refers to the induction of an immune response by an injected preparation of PEG-modified or unmodified uricase (the antigen), while "antigenicity" refers to the reaction of an antigen with preexisting antibodies. Collectively, antigenicity and immunogenicity are referred to as "immunoreactivity." In previous studies of PEG-uricase, immunoreactivity is assessed by a variety of methods, including: 1) the reaction in vitro of PEG-uricase with preformed antibodies; 2) measurements of induced antibody synthesis; and 3) accelerated clearance rates after repeated injections.

Previous attempts to eliminate the immunogenicity of uricases from several sources by coupling various numbers of strands of PEG through various linkers have met with limited success. PEG-uricases were first disclosed by F F Davis and by Y Inada and their colleagues. Davis, et al., (1978); U.S. Pat. No. 4,179,337; Nishimura, et al., (1979); Japanese Patents 55-99189 and 62-55079, each incorporated herein by reference in its entirety. The conjugate disclosed in U.S. Pat. No. 4,179,337 is synthesized by reacting uricase of unspecified origin with a 2.000-fold molar excess of 750 dalton PEG, indicating that a large number of polymer molecules is likely to have been attached to each uricase subunit. U.S. Pat. No. 4,179,337 discloses the coupling of either PEG or polypropylene glycol) with molecular weights of 500 to 20,000 daltons, preferably about 500 to 5,000 daltons, to provide active, water-soluble, non-immunogenic conjugates of various polypeptide hormones and enzymes including oxidoreductases, of which uricase is one of three examples. In addition, U.S. Pat. No. 4,179,337 emphasizes the coupling of 10 to 100 polymer strands per molecule of enzyme, and the retention of at least 40% of enzymatic activity. No test results were reported for the extent of coupling of PEG to the available amino groups of uricase, the residual specific uricolytic activity, or the immunoreactivity of the conjugate.

In previous publications, significant decreases in uricolytic activity measured in vitro were caused by coupling various numbers of strands of PEG to uricase from *Candida utilis*. Coupling a large number of strands of 5 kDa PEG to porcine liver uricase gave similar results, as described in both the Chen publication and a symposium report by the same group. Chen, et al., (1981); Davis, et al., (1978).

In seven previous studies, the immunoreactivity of uricase is reported to be decreased by PEGylation and was eliminated in five other studies. In three of the latter five studies, the elimination of immunoreactivity is associated with profound decreases in uricolytic activity—to at most 15%, 28%, or 45% of the initial activity. Nishimura, et al., (1979) (15% activity); Chen, et al., (1981) (28% activity); Nishimura, et al., (1981) (45% activity). In the fourth report, PEG is reported to be coupled to 61% of the available lysine residues, but the residual specific activity is not stated. Abuchowski, et al., (1981). However, a research team that included two of the same scientists and used the same methods reported elsewhere that this extent of coupling left residual activity of only 23-28%. Chen, et al., (1981). The 1981 publications of Abuchowski et al., and Chen et al., indicate that to reduce the immunogenicity of uricase substantially, PEG must be coupled to approximately 60% of the available lysine residues. The fifth publication in which the immunoreactivity of uricase is reported to have been eliminated does not disclose the extent of PEG coupling, the residual uricolytic activity, or the nature of the PEG-protein linkage. Veronese, F M, et al., (1997) in J M Harris, et al., (Eds.), Poly(ethylene glycol) Chemistry and Biological Applications. ACS Symposium Series 680 (pp. 182-192) Washington, D.C.: American Chemical Society, incorporated herein by reference in its entirety.

Conjugation of PEG to a smaller fraction of the lysine residues in uricase reduced but did not eliminate its immunoreactivity in experimental animals. Tsuji, J, et al., (1985) *Int J Immunopharmacol* 7:725-730, incorporated herein by reference in its entirety (28-45% of the amino groups coupled); Yasuda, Y, et al., (1990) *Chem Pharm Bull* 38:2053-2056, incorporated herein by reference in its entirety (38% of the amino groups coupled). The residual uricolytic activities of the corresponding adducts ranged from <33% (Tsuji, et al.) to 60% (Yasuda, et al.) of their initial values. Tsuji, et al., synthesized PEG-uricase conjugates with 7.5 kDa and 10 kDa PEGs, in addition to 5 kDa PEG. All of the resultant conjugates are somewhat immunogenic and antigenic, while displaying markedly reduced enzymatic activities.

A PEGylated preparation of uricase from *Candida utilis* that is safely administered twice to each of five humans is reported to have retained only 11% of its initial activity. Davis, et al., (1981). Several years later, PEG-modified uricase from *Arthrobacter protoformiae* was administered four times to one patient with advanced lymphoma and severe hyperuricemia. Chua, et al., (1988). While the residual activity of that enzyme preparation was not measured, Chua, et al., demonstrated the absence of anti-uricase antibodies in the patient's serum 26 days after the first PEG-uricase injection, using an enzyme-linked immunosorbent assay (ELISA).

Previous studies of PEGylated uricase show that catalytic activity is markedly depressed by coupling a sufficient number of strands of PEG to decrease its immunoreactivity substantially. Furthermore, most previous preparations of PEG-uricase are synthesized using PEG activated with cyanuric chloride, a triazine derivative (2,4,6-trichloro-1,3,5-triazine)

that has been shown to introduce new antigenic determinants and to induce the formation of antibodies in rabbits. Tsuji, et al., (1985).

Japanese Patent No. 3-148298 to A Sano, et al., incorporated herein by reference in its entirety, discloses modified proteins, including uricase, derivatized with PEG having a molecular weight of 1-12 kDa that show reduced antigenicity and "improved prolonged" action, and methods of making such derivatized peptides. However, there are no disclosures regarding strand counts, enzyme assays, biological tests or the meaning of "improved prolonged." Japanese Patents 55-99189 and 62-55079, each incorporated herein by reference in its entirety, both to Y Inada, disclose uricase conjugates prepared with PEG-triazine or bis-PEG-triazine (denoted as $PEG_2$), respectively. See Nishimura, et al., (1979 and 1981). In the first type of conjugate, the molecular weights of the PEGs are 2 kDa and 5 kDa, while in the second, only 5 kDa PEG is used. Nishimura, et al., (1979) reported the recovery of 15% of the uricolytic activity after modification of 43% of the available lysines with linear 5 kDa PEG, while Nishimura, et al., (1981) reported the recovery of 31% or 45% of the uricolytic activity after modification of 46% or 36% of the lysines, respectively, with $PEG_2$.

Previously studied uricase proteins were either natural or recombinant proteins. However, studies using SDS-PAGE and/or Western techniques revealed the presence of unexpected low molecular weight peptides which appear to be degradation products and increase in frequency over time. The present invention is related to mutant recombinant uricase proteins having truncations and enhanced structural stability.

SUMMARY OF THE INVENTION

The present invention provides novel recombinant uricase proteins. In one embodiment, the proteins of the invention contemplated are truncated and have mutated amino acids relative to naturally occurring uricase proteins. In particular embodiments, the mutations are at or around the areas of amino acids 7, 46, 291, and 301. Conservative mutations anywhere in the peptide are also contemplated as a part of the invention.

The subject invention provides a mutant recombinant uricase, wherein the uricase has been truncated by 1-20 amino acids and retains the uricolytic activity of the naturally occurring uricase. The truncations are at or around the sequence termini such that the protein may contain the ultimate amino acids. These mutations and truncations may enhance stability of the protein comprising such mutations.

In another embodiment, the present invention to provides a means for metabolizing uric acid comprising a novel recombinant uricase protein having uricolytic activity. Uricolytic activity is used herein to refer to the enzymatic conversion of uric acid to allantoin.

The subject invention further provides a host cell with the capacity for producing a uricase that has been truncated by 1-20 amino acids, and has mutated amino acids and retains uricolytic activity.

In an embodiment, an isolated truncated mammalian uricase is provided comprising a mammalian uricase amino acid sequence truncated at the amino terminus or the carboxy terminus or both the amino and carboxy termini by about 1-13 amino acids and further comprising an amino acid substitution at about position 46. In particular embodiments, the uricase comprises an amino terminal amino acid, wherein the amino terminal amino acid is alanine, glycine, proline, serine, or threonine. Also provided is a uricase wherein there is a substitution at about position 46 with threonine or alanine. In an embodiment, the uricase comprises the amino acid sequence of SEQ ID NO. 8. In an embodiment, the uricase is conjugated with a polymer to form, for example, a polyethylene glycol-uricase conjugate. In particular embodiments, polyethylene glycol-uricase conjugates comprise 2 to 12 polyethylene glycol molecules on each uricase subunit, preferably 3 to 10 polyethylene glycol molecules per uricase subunit. In particular embodiments, each polyethylene glycol molecule of the polyethylene glycol-uricase conjugate has a molecular weight between about 1 kD and 100 kD; about 1 kD and 50 kD; about 5 kD and 20 kD; or about 10 kD. Also provided are pharmaceutical compositions comprising the uricase of the invention, including the polyethylene glycol-uricase conjugate. In an embodiment, the pharmaceutical composition is suitable for repeated administration.

Also provided is a method of reducing uric acid levels in a biological fluid of a subject in need thereof, comprising administering the pharmaceutical composition comprising the uricase of the invention. In a particular embodiment, the biological fluid is blood.

In an embodiment, the uricase comprises a peptide having the sequence of position 44 to position 56 of Pig-KS-ΔN (SEQ ID NO. 14).

In an embodiment, the uricase protein comprises an N-terminal methionine. In a particular embodiment, the uricase comprises the amino acid sequence of SEQ ID NO. 7.

Also provided are isolated nucleic acids comprising a nucleic acid sequence which encodes a uricase of the invention, for example, uricases having or comprising the amino acid sequences of SEQ ID NO. 7, SEQ ID NO. 8, SEQ ID NO. 12 or SEQ ID NO. 13. In an embodiment, the isolated nucleic acid is operatively linked to a heterologous promoter, for example, the osmB promoter. Also provided are vectors comprising uricase encoding nucleic acids, and host cells comprising such vectors. In an embodiment, the nucleic acid has the sequence of SEQ ID NO. 7. Also provided is a method for producing a uricase comprising the steps of culturing such a host cell under conditions such that uricase is expressed by the host cell and isolating the expressed uricase.

BRIEF DESCRIPTION OF THE DRAWINGS

FIG. 2 depicts the DNA and the deduced amino acid sequences of Pig-KS-ΔN uricase (SEQ ID NO. 9 and SEQ ID NO. 7, respectively). The amino acid numbering in FIG. 2 is relative to the complete pig uricase sequence. Following the initiator methionine residue, a threonine replaces aspartic acid 7 of the pig uricase sequence. The restriction sites that are used for the various steps of subcloning are indicated. The 3' untranslated sequence is shown in lowercase letters. The translation stop codon is indicated by an asterisk.

FIG. 3 shows relative alignment of the deduced amino acid sequences of the various recombinant pig (SEQ ID NO. 11), PBC-ΔNC (SEQ ID NO. 12), and Pig-KS-ΔN (SEQ ID NO. 7) uricase sequences. The asterisks indicate the positions in which there are differences in amino acids in the Pig-KS-ΔN as compared to the published pig uricase sequence; the circles indicate positions in which there are differences in amino acids in Pig-KS-ΔN as compared to PBC-ΔNC. Dashed lines indicate deletion of amino acids.

DETAILED DESCRIPTION OF THE INVENTION

Figure 1:
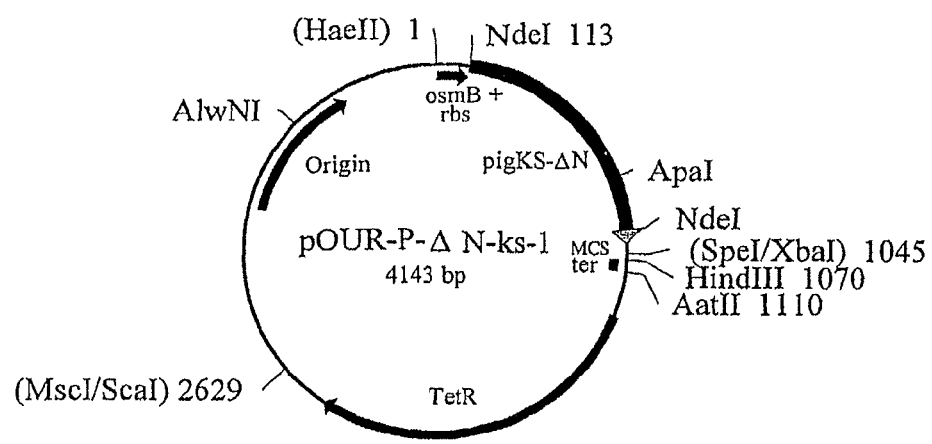
FIG. 1 illustrates the structure of plasmid pOUR-P-ΔN-ks-1. Numbers next to restriction sites indicate nucleotide position, relative to HaeII site, designated as 1. Restriction sites which are lost during cloning are marked in parenthesis.

Previous studies teach that when a significant reduction in the immunogenicity and/or antigenicity of uricase is achieved by PEGylation, it is invariably associated with a substantial loss of uricolytic activity. The safety, convenience and cost-effectiveness of biopharmaceuticals are all adversely impacted by decreases in their potencies and the resultant need to increase the administered dose. Thus, there is a need for a safe and effective alternative means for lowering elevated levels of uric acid in body fluids, including blood. The present invention provides a mutant recombinant uricase, wherein the uricase has been truncated by 1-20 amino acids at either the amino terminus or the carboxy terminus, or both, and substantially retains uricolytic activity of the naturally occurring uricase.

Uricase, as used herein, includes individual subunits, as well as the tetramer, unless otherwise indicated.

Mutated uricase, as used herein, refers to uricase molecules having amino acids exchanged with other amino acids.

A conservative mutation, as used herein, is a mutation of one or more amino acids, at or around a position, that does not substantially alter the protein's behavior. In a preferred embodiment, the uricase comprising at least one conservative mutation has the same uricase activity as does uricase without such mutation. In alternate embodiments, the uricase comprising at least one conservative mutation has substantially the same uricase activity, within 5% of the activity, within 10% of the activity, or within 30% of the activity of uricase without such mutation.

Conservative amino acid substitution is defined as a change in the amino acid composition by way of changing amino acids of a peptide, polypeptide or protein, or fragment thereof. In particular embodiments, the uricase has one, two, three or four conservative mutations. The substitution is of amino acids with generally similar properties (e.g., acidic, basic, aromatic, size, positively or negatively charged, polar, non-polar) such that the substitutions do not substantially alter peptide, polypeptide or protein characteristics (e.g., charge, IEF, affinity, avidity, conformation, solubility) or activity. Typical substitutions that may be performed for such conservative amino acid substitution may be among the groups of amino acids as follows:

glycine (G), alanine (A), valine (V), leucine (L) and isoleucine (I)
aspartic acid (D) and glutamic acid (E)
alanine (A), serine (S) and threonine (T)
histidine (H), lysine (K) and arginine (R)
asparagine (N) and glutamine (Q)
phenylalanine (F), tyrosine (Y) and tryptophan (W)

The protein having one or more conservative substitutions retains its structural stability and can catalyze a reaction even though its DNA sequence is not the same as that of the original protein.

Truncated uricase, as used herein, refers to uricase molecules having shortened primary amino acid sequences. Amongst the possible truncations are truncations at or around the amino and/or carboxy termini. Specific truncations of this type may be such that the ultimate amino acids (those of the amino and/or carboxy terminus) of the naturally occurring protein are present in the truncated protein. Amino terminal truncations may begin at position 1, 2, 3, 4, 5 or 6. Preferably, the amino terminal truncations begin at position 2, thereby leaving the amino terminal methionine. This methionine may be removed by post-translational modification. In particular embodiments, the amino terminal methionine is removed after the uricase is produced. In a particular embodiment, the methionine is removed by endogenous bacterial aminopeptidase.

A truncated uricase, with respect to the full length sequence, has one or more amino acid sequences excluded. A protein comprising a truncated uricase may include any amino acid sequence in addition to the truncated uricase sequence, but does not include a protein comprising a uricase sequence containing any additional sequential wild type amino acid sequence. In other words, a protein comprising a truncated uricase wherein the truncation begins at position 6 (i.e., the truncated uricase begins at position 7) does not have, immediately upstream from the truncated uricase, whatever amino acid that the wild type uricase has at position 6.

Unless otherwise indicated by specific reference to another sequence or a particular SEQ ID NO., reference to the numbered positions of the amino acids of the uricases described herein is made with respect to the numbering of the amino acids of the pig uricase sequence. The amino acid sequence of pig uricase and the numbered positions of the amino acids comprising that sequence may be found in FIG. 3. As used herein, reference to amino acids or nucleic acids "from position X to position Y" means the contiguous sequence beginning at position X and ending at position Y, including the amino acids or nucleic acids at both positions X and Y.

Uricase genes and proteins have been identified in several mammalian species, for example, pig, baboon, rat, rabbit, mouse, and rhesus monkey. The sequences of various uricase proteins are described herein by reference to their public data base accession numbers, as follows: gi|50403728|sp|25689; gi|20513634|dbj|BAB91555.1; gi|176610|AAA35395.1; gi|20513654|dbj|BAB91557.1; gi|47523606|ref|NP_999435.1; gi|6678509|ref|NP_033500.1; gi|57463|emb|CAA31490.1; gi|20127395|ref|NP_446220.1; gi|137107|sp|P11645; gi|51458661|ref|XP_497688.1; gi|207619|gb|AAA42318.1; gi|26340770|dbj|BAC34047.1; and gi|57459|emb|CAA30378.1. Each of these sequences and their annotations in the public databases accessible through the National Center for Biotechnology Information (NCBI) is incorporated by reference in its entirety.

In an embodiment of the invention, the uricase is truncated by 4-13 amino acids at its amino terminus. In an embodiment of the invention, the uricase is truncated by 4-13 amino acids at its carboxy terminus. In an embodiment of the invention, the uricase is truncated by 4-13 amino acids at both its carboxy and amino termini.

In an embodiment of the invention, the uricase is truncated by 6 amino acids at its amino terminus. In an embodiment of the invention, the uricase is truncated by 6 amino acids at its carboxy terminus. In an embodiment of the invention, the uricase is truncated by 6 amino acids at both its carboxy and amino termini.

In a particular embodiment, the uricase protein comprises the amino acid sequence from position 13 to position 292 of the amino acid sequence of pig uricase (SEQ ID NO. 11). In a particular embodiment, the uricase protein comprises the amino acid sequence from position 8 to position 287 of the amino acid sequence of PBC-ΔNC (SEQ ID NO. 12). In a particular embodiment, the uricase protein comprises the amino acid sequence from position 8 to position 287 of the amino acid sequence of Pig-KS-ΔN (SEQ ID NO. 7).

In another embodiment, the uricase protein comprises the amino acid sequence from position 44 to position 56 of Pig-KS-ΔN (SEQ ID NO. 14). This region of uricase has homology to sequences within the tunneling fold (T-fold) domain of uricase, and has within it a mutation at position 46 with respect to the native pig uricase sequence. This mutation surprisingly does not significantly alter the uricase activity of the protein.

In an embodiment of the invention, amino acids at or around any of amino acids 7, 46, and 291, and 301 are mutated. In a preferred embodiment of the invention, amino acids 7, 46, and 291, and 301, themselves, are mutated.

In particular embodiments, the protein is encoded by a nucleic acid that encodes an N-terminal methionine. Preferably, the N-terminal methionine is followed by a codon that allows for removal of this N-terminal methionine by bacterial methionine aminopeptidase (MAP). (Ben-Bassat and Bauer (1987) Nature 326:315, incorporated herein by reference in its entirety). Amino acids allowing the most complete removal of the N-terminal methionine are alanine, glycine, proline, serine, and threonine.

In an embodiment of the invention, the amino acids at or around positions 7 and/or 46 are substituted by threonine. Surprisingly, the enzymatic activity of truncated uricases prepared with these mutations is similar to that of the non-truncated enzyme. In a further embodiment of the invention, the amino acid mutations comprise threonine, threonine, lysine, and serine, at positions 7, 46, 291, and 301, respectively.

The truncated mammalian uricases disclosed herein may further comprise a methionine at the amino terminus. The penultimate amino acid may one that allows removal of the N-terminal methionine by bacterial methionine aminopeptidase (MAP). Amino acids allowing the most complete removal of the N-terminal methionine are alanine, glycine, proline, serine, and threonine. In a particular embodiment, the uricase comprises two amino terminal amino acids, wherein the two amino terminal amino acids are a methionine followed by an amino acid selected from the group consisting of alanine, glycine, proline, serine, and threonine.

In another embodiment of the invention, the substituted amino acids have been replaced by threonine.

In an embodiment of the invention, the uricase is a mammalian uricase.

In an embodiment of the invention, the mammalian uricase comprises the sequence of porcine, bovine, ovine or baboon liver uricase.

In an embodiment of the invention, the uricase is a chimeric uricase of two or more mammalian uricases.

In an embodiment of the invention, the mammalian uricases are selected from porcine, bovine, ovine, or baboon liver uricase.

In an embodiment of the invention, the uricase comprises the sequence of SEQ ID NO. 8.

In another embodiment of the invention, the uricase comprises the sequence of SEQ ID NO. 13.

The subject invention provides uricase encoding nucleic acids comprising the sequence of SEQ ID NO. 10.

In an embodiment of the invention, the uricase comprises fungal or microbial uricase.

In an embodiment of the invention, the fungal or microbial uricase is *Aspergillus flavus, Arthrobacter globiformis* or *Candida utilis* uricase.

In an embodiment of the invention, the uricase comprises an invertebrate uricase.

In an embodiment of the invention, the invertebrate uricase *Drosophila melanogaster* or *Drosophila pseudoobscura* uricase.

In an embodiment of the invention, the uricase comprises plant uricase.

In an embodiment of the invention, the plant uricase is *Glycine max* uricase of root nodules.

The subject invention provides a nucleic acid sequence encoding the uricase.

The subject invention provides a vector comprising the nucleic acid sequence.

In a particular embodiment, the uricase is isolated. In a particular embodiment, the uricase is purified. In particular embodiments, the uricase is isolated and purified.

The subject invention provides a host cell comprising a vector.

The subject invention provides a method for producing the nucleic acid sequence, comprising modification by PCR (polymerase chain reaction) techniques of a nucleic acid sequence encoding a nontruncated uricase. One skilled in the art knows that a desired nucleic acid sequence is prepared by PCR via synthetic oligonucleotide primers, which are complementary to regions of the target DNA (one for each strand) to be amplified. The primers are added to the target DNA (that need not be pure), in the presence of excess deoxynucleotides and Taq polymerase, a heat stable DNA polymerase. In a series (typically 30) of temperature cycles, the target DNA is repeatedly denatured (around 90° C.), annealed to the primers (typically at 50-60° C.) and a daughter strand extended from the primers (72° C.). As the daughter strands themselves act as templates for subsequent cycles, DNA fragments matching both primers are amplified exponentially, rather than linearly.

The subject invention provides a method for producing a mutant recombinant uricase comprising transfecting a host cell with the vector, wherein the host cell expresses the uricase, isolating the mutant recombinant uricase from the host cell, isolating the purified mutant recombinant uricase using, for example, chromatographic techniques, and purifying the mutant recombinant uricase. For example, the uricase can be made according to the methods described in International Patent Publication No. WO 00/08196, incorporated herein by reference in its entirety.

The uricase may be isolated and/or purified by any method known to those of skill in the art. Expressed polypeptides of this invention are generally isolated in substantially pure form. Preferably, the polypeptides are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography. The uricase is preferably isolated using a cationic surfactant, for example, cetyl pyridinium chloride (CPC) according to the method described in copending United States patent application filed on Apr. 11, 2005 having application No. 60/670,520, entitled Purification Of Proteins With Cationic Surfactant, incorporated herein by reference in its entirety.

In a preferred embodiment, the host cell is treated so as to cause the expression of the mutant recombinant uricase. One skilled in the art knows that transfection of cells with a vector is usually accomplished using DNA precipitated with calcium ions, though a variety of other methods can be used (e.g. electroporation).

In an embodiment of the invention, the vector is under the control of an osmotic pressure sensitive promoter. A promoter is a region of DNA to which RNA polymerase binds before initiating the transcription of DNA into RNA. An osmotic pressure sensitive promoter initiates transcription as a result of increased osmotic pressure as sensed by the cell.

In an embodiment of the invention, the promoter is a modified osmB promoter.

In particular embodiments, the uricase of the invention is a uricase conjugated with a polymer.

In an embodiment of the invention, a pharmaceutical composition comprising the uricase is provided. In one embodiment, the composition is a solution of uricase. In a preferred embodiment, the solution is sterile and suitable for injection. In one embodiment, such composition comprises uricase as a solution in phosphate buffered saline. In one embodiment, the composition is provided in a vial, optionally having a rubber injection stopper. In particular embodiments, the composition comprises uricase in solution at a concentration of from 2 to 16 milligrams of uricase per milliliter of solution, from 4 to 12 milligrams per milliliter or from 6 to 10 milligrams per milliliter. In a preferred embodiment, the composition comprises uricase at a concentration of 8 milligrams per milliliter. Preferably, the mass of uricase is measured with respect to the protein mass.

Effective administration regimens of the compositions of the invention may be determined by one of skill in the art. Suitable indicators for assessing effectiveness of a given regimen are known to those of skill in the art. Examples of such indicators include normalization or lowering of plasma uric acid levels (PUA) and lowering or maintenance of PUA to 6.8 mg/dL or less, preferably 6 mg/dL or less. In a preferred embodiment, the subject being treated with the composition of the invention has a PUA of 6 mg/ml or less for at least 70%, at least 80%, or at least 90% of the total treatment period. For example, for a 24 week treatment period, the subject preferably has a PUA of 6 mg/ml or less for at least 80% of the 24 week treatment period, i.e., for at least a time equal to the amount of time in 134.4 days (24 weeks×7 days/week× 0.8=134.4 days).

In particular embodiments, 0.5 to 24 mg of uricase in solution is administered once every 2 to 4 weeks. The uricase may be administered in any appropriate way known to one of skill in the art, for example, intravenously, intramuscularly or subcutaneously. Preferably, when the administration is intravenous, 0.5 mg to 12 mg of uricase is administered. Preferably, when the administration is subcutaneous, 4 to 24 mg of uricase is administered. In a preferred embodiment, the uricase is administered by intravenous infusion over a 30 to 240 minute period. In one embodiment, 8 mg of uricase is administered once every two weeks. In particular embodiments, the infusion can be performed using 100 to 500 mL of saline solution. In a preferred embodiment, 8 mg of uricase in solution is administered over a 120 minute period once every 2 weeks or once every 4 weeks; preferably the uricase is dissolved in 250 mL of saline solution for infusion. In particular embodiments, the uricase administrations take place over a treatment period of 3 months, 6 months, 8 months or 12 months. In other embodiments, the treatment period is 12 weeks, 24 weeks, 36 weeks or 48 weeks. In a particular embodiment, the treatment period is for an extended period of time, e.g., 2 years or longer, for up to the life of subject being treated. In addition, multiple treatment periods may be utilized interspersed with times of no treatment, e.g., 6 months of treatment followed by 3 months without treatment, followed by 6 additional months of treatment, etc.

In certain embodiments, anti-inflammatory compounds may be prophylactically administered to eliminate or reduce the occurrence of infusion reactions due to the administration of uricase. In one embodiment, at least one corticosteroid, at least one antihistamine, at least one NSAID, or combinations thereof are so administered. Useful corticosteroids include betamethasone, budesonide, cortisone, dexamethasone, hydrocortisone, methylprednisolone, prednisolone, prednisone and triamcinolone. Useful NSAIDs include ibuprofen, indomethacin, naproxen, aspirin, acetaminophen, celecoxib and valdecoxib. Useful antihistamines include azatadine, brompheniramine, cetirizine, chlorpheniramine, clemastine, cyproheptadine, desloratadine, dexchlorpheniramine, dimenhydrinate, diphenhydramine, doxylamine, fexofenadine, hydroxyzine, loratadine and phenindamine.

In a preferred embodiment, the antihistamine is fexofenadine, the NSAID is acetaminophen and the corticosteroid is hydrocortisone and/or prednisone. Preferably, a combination of all three (not necessarily concomitantly) are administered prior to infusion of the uricase solution. In a preferred embodiment, the NSAID and antihistamine are administered orally 1 to 4 hours prior to uricase infusion. A suitable dose of fexofenadine includes about 30 to about 180 mg, about 40 to about 150 mg, about 50 to about 120 mg, about 60 to about 90 mg, about 60 mg, preferably 60 mg. A suitable dose of acetaminophen includes about 500 to about 1500 mg, about 700 to about 1200 mg, about 800 to about 1100 mg, about 1000 mg, preferably 1000 mg. A suitable dose of hydrocortisone includes about 100 to about 500 mg, about 150 to about 300 mg, about 200 mg, preferably 200 mg. In one embodiment, the antihistamine is not diphenhydramine. In another embodiment, the NSAID is not acetaminophen. In a preferred embodiment, 60 mg fexofenadine is administered orally the night before uricase infusion; 60 mg fexofenadine and 1000 mg of acetaminophen are administered orally the next morning, and finally, 200 mg hydrocortisone is administered just prior to the infusion of the uricase solution. In one embodiment, prednisone is administered the day, preferably in the evening, prior to uricase administration. An appropriate dosage of prednisone includes 5 to 50 mg, preferably 20 mg. In certain embodiments, these prophylactic treatments to eliminate or reduce the occurrence of infusion reactions are utilized for subjects receiving or about to receive uricase, including PEGylated uricase and non-PEGylated uricase. In particular embodiments, these prophylactic treatments are utilized for subjects receiving or about to receive therapeutic peptides other than uricase, wherein the other therapeutic peptides are PEGylated or non-PEGylated.

In an embodiment of the invention, the pharmaceutical composition comprises a uricase that has been modified by conjugation with a polymer, and the modified uricase retains uricolytic activity. In a particular embodiment, polymer-uricase conjugates are prepared as described in International Patent Publication No. WO 01/59078 and U.S. application Ser. No. 09/501,730, incorporated herein by reference in their entireties.

In an embodiment of the invention, the polymer is selected from the group comprising polyethylene glycol, dextran, polypropylene glycol, hydroxypropylmethyl cellulose, carboxymethylcellulose, polyvinyl pyrrolidone, and polyvinyl alcohol.

In an embodiment of the invention, the composition comprises 2-12 polymer molecules on each uricase subunit, preferably 3 to 10 polymer molecules per uricase subunit.

In an embodiment of the invention, each polymer molecule has a molecular weight between about 1 kD and about 100 kD.

In another embodiment of the invention, each polymer molecule has a molecular weight between about 1 kD and about 50 kD. In a preferred embodiment of the invention, each polymer molecule has a molecular weight of between about 5 kD and about 20 kD, about 8 kD and about 15 kD, about 10 kD and 12 kD, preferably about 10 kD. In a preferred embodiment, each polymer molecule has a molecular weight of about 5 kD or about 20 kD. In an especially preferred embodiment of the invention, each polymer molecule has a molecular weight of 10 kD. Mixtures of different weight molecules are also contemplated. In an embodiment of the invention, the composition is suitable for repeated administration of the composition.

In a particular embodiment, conjugation of the uricase to the polymer comprises linkages selected from the group consisting of urethane linkages, secondary amine linkages, and amide linkages.

The subject invention provides a cell with the capacity for producing a uricase having an amino acid sequence of recombinant uricase, wherein the uricase has been truncated by 1-20 amino acids, and has mutated amino acids and uricolytic activity.

The subject invention provides a means for metabolizing uric acid using the uricase.

The subject invention provides a use of a composition of uricase for reducing uric acid levels in a biological fluid.

In an embodiment of the invention, the composition of uricase is used for reducing uric acid in a biological fluid comprising blood.

Also provided are novel nucleic acid molecules encoding uricase polypeptides. The manipulations which result in their production are well known to the one of skill in the art. For example, uricase nucleic acid sequences can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a uricase, care should be taken to ensure that the modified gene remains within the appropriate translational reading frame, uninterrupted by translational stop signals. Additionally, the uricase-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, *J. Biol. Chem.* 253:6551), use of TAB® linkers (Pharmacia) (as described in U.S. Pat. No. 4,719,179), etc.

The nucleotide sequence coding for a uricase protein can be inserted into an appropriate expression vector, i.e., a vector which contains the necessary elements for the transcription and translation of the inserted protein-coding sequence. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities.

Depending on the host-vector system utilized, any one of a number of suitable transcription and translation elements may be used.

Any of the methods known for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding uricase protein may be regulated by a second nucleic acid sequence so that uricase protein is expressed in a host transformed with the recombinant DNA molecule. For example, expression of uricase may be controlled by any promoter/enhancer element known in the art. Promoters which may be used to control uricase expression include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionine gene (Brinster et al., 1982, Nature 296:39-42); prokaryotic expression vectors such as the β-lactamase promoter (VIIIa-Kamaroff, et al., 1978, Proc. Natl. Acad. Sci. U.S.A. 75:3727-3731), the tac promoter (DeBoer, et al., 1983, Proc. Natl. Acad. Sci. U.S.A. 80:21-25), and the osmB promoter. In particular embodiments, the nucleic acid comprises a nucleic acid sequence encoding the uricase operatively linked to a heterologous promoter.

Once a particular recombinant DNA molecule comprising a nucleic acid sequence encoding is prepared and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered uricase protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. Different vector/host expression systems may effect processing reactions such as proteolytic cleavages to different extents.

In particular embodiments of the invention, expression of uricase in *E. coli* is preferably performed using vectors which comprise the osmB promoter.

EXAMPLES

Example 1

Construction of Gene and Expression Plasmid for Uricase Expression

Recombinant porcine uricase (urate oxidase), Pig-KS-ΔN (amino terminus truncated pig uricase protein replacing amino acids 291 and 301 with lysine and serine, respectively) was expressed in *E. coli* K-12 strain W3 110 F–. A series of plasmids was constructed culminating in pOUR-P-ΔN-ks-1, which upon transformation of the *E. coli* host cells was capable of directing efficient expression of uricase.
Isolation and Subcloning of Uricase cDNA From Pig and Baboon Liver Uricase cDNAs were prepared from pig and baboon livers by isolation and subcloning of the relevant RNA. Total cellular RNA was extracted from pig and baboon livers (Erlich, H. A. (1989). PCR Technology; Principles and Application for DNA Amplification; Sambrook, J., et al. (1989). Molecular Cloning: A Laboratory Manual, 2nd edition; Ausubel, F. M. et al. (1998). Current protocols in molecular Biology), then reverse-transcribed using the First-Strand cDNA Synthesis Kit (Pharmacia Biotech). PCR amplification was performed using Taq DNA polymerase (Gibco BRL, Life Technologies).

The synthetic oligonucleotide primers used for PCR amplification of pig and baboon urate oxidases (uricase) are shown in Table 1.

TABLE 1

Primers For PCR Amplification Of Uricase cDNA

| Pig liver uricase: | |
|---|---|
| sense | 5' gcgcgaattccATGGCTCATTACCGTAATGACTACA 3'<br>(SEQ ID NO. 1) |
| anti-sense | 5' gcgctctagaagcttccatggTCACAGCCTTGAAGTCAGC 3'<br>(SEQ ID NO. 2) |

| Baboon (D3H) liver uricase: | |
|---|---|
| sense | 5' gcgcgaattccATGGCCCACTACCATAACAACTAT 3'<br>(SEQ ID NO. 3) |
| anti-sense | 5' gcgcccatggtctagaTCACAGTCTTGAAGACAACTTCCT 3'<br>(SEQ ID NO. 4) |

Restriction enzyme sequences, introduced at the ends of the primers and shown in lowercase in Table 1, were sense EcoRI and NcoI (pig and baboon) and anti-sense NcoI, HindIII and XbaI (pig), XbaI and NcoI (baboon). In the baboon sense primer, the third codon GAC (aspartic acid) present in baboon uricase was replaced with CAC (histidine), the codon that is present at this position in the coding sequence of the human urate oxidase pseudogene. The recombinant baboon uricase construct generated using these primers is named D3H Baboon Uricase.

The pig uricase PCR product was digested with EcoRI and HindIII and cloned into pUC18 to create pUC18-Pig Uricase. The D3H Baboon Uricase PCR product was cloned directly into PCR®II vector (TA Cloning Vector pCRTMII), using TA Cloning® biochemical laboratory kits for cloning of amplified nucleic acids (Invitrogen, Carlsbad, Calif.), creating PCR®II-D3H Baboon Uricase.

Ligated cDNAs were used to transform *E. coli* strain XL1-Blue (Stratagene, La Jolla, Calif.). Plasmid DNA containing cloned uricase cDNA was prepared, and clones which possess the published uricase DNA coding sequences (except for the D3H substitution in baboon uricase, shown in Table 1) were selected and isolated. In the PCR®II-D3H Baboon Uricase clone chosen, the PCR®II sequences were next to the uricase stop codon, resulting from deletion of sequences introduced by PCR. As a consequence, the XbaI and NcoI restriction sites from the 3' untranslated region were eliminated, thus allowing directional cloning using NcoI at the 5' end of the PCR product and BamHI which is derived from the PCR®II vector.
Subcloning of Uricase cDNA Into pET Expression Vectors
Baboon Uricase Subcloning The D3H baboon cDNA containing full length uricase coding sequence was introduced into pET-3d expression vector (Novagen, Madison, Wis.). The PCR®II-D3H Baboon Uricase was digested with NcoI and BamHI, and the 960 bp fragment was isolated. The expression plasmid pET-3d was digested with NcoI and BamHI, and the 4600 bp fragment was isolated. The two fragments were ligated to create pET-3d-D3H-Baboon.
Pig-Baboon Chimera Uricase Subcloning Pig-baboon chimera (PBC) uricase was constructed in order to gain higher expression, stability, and activity of the recombinant gene. PBC was constructed by isolating the 4936 bp NcoI-ApaI fragment from pET-3d-D3H-Baboon clone and ligating the isolated fragment with the 624 bp NcoI-ApaI fragment isolated from pUC18-Pig Uricase, resulting in the formation of pET-3d-PBC. The PBC uricase cDNA consists of the pig uricase codons 1-225 joined in-frame to codons 226-304 of baboon uricase.

Pig-KS Uricase Subcloning

Pig-KS uricase was constructed in order to add one lysine residue, which may provide an additional PEGylation site. KS refers to the amino acid insert of lysine into pig uricase, at position 291, in place of arginine (R291K). In addition, the threonine at position 301 was replaced with serine (T301 S). The PigKS uricase plasmid was constructed by isolating the 4696 bp NcoI-NdeI fragment of pET-3d-D3H-Baboon, and then it was ligated with the 864 bp NcoI-NdeI fragment isolated from pUC18-Pig Uricase, resulting in the formation of pET-3d-PigKS. The resulting PigKS uricase sequence consists of the pig uricase codons 1-288 joined in-frame to codons 289-304 of baboon uricase.

Subcloning of Uricase Sequence Under the Regulation of the osmB Promoter

The uricase gene was subcloned into an expression vector containing the osmB promoter (following the teaching of U.S. Pat. No. 5,795,776, incorporated herein by reference in its entirety). This vector enabled induction of protein expression in response to high osmotic pressure or culture aging. The expression plasmid pMFOA-18 contained the osmB promoter, a ribosomal binding site sequence (rbs) and a transcription terminator sequence (ter). It confers ampicillin resistance (AmpR) and expresses the recombinant human acetylcholine esterase (AChE).

Subcloning of D3H-Baboon Uricase

The plasmid pMFOA-18 was digested with NcoI and BamHI, and the large fragment was isolated. The construct pET-3d-D3H-Baboon was digested with NcoI and BamHI and the 960 bp fragment, which included the D3H Baboon Uricase gene is isolated. These two fragments were ligated to create pMFOU18.

The expression plasmid pMFXT133 contained the osmB promoter, a rbs (*E. coli* deo operon), ter (*E. coli* TrypA), the recombinant factor Xa inhibitor polypeptide (FxaI), and it 2 5 conferred the tetracycline resistance gene (TetR). The baboon uricase gene was inserted into this plasmid in order to exchange the antibiotic resistance genes. The plasmid pMFOU18 was digested with NcoI, filled-in, then it was digested with XhoI, and a 1030 bp fragment was isolated. The plasmid pMFXT133 was digested with NdeI, filled-in, then it was digested with XhoI, and the large fragment was isolated. The two fragments were ligated to create the baboon uricase expression vector, pURBA16.

Subcloning of the Pig Baboon Chimera Uricase

The plasmid pURBA16 was digested with ApaI and AlwNI, and the 2320 bp fragment was isolated. The plasmid pMFXT133 was digested with NdeI, filled-in, then it was digested with AlwNI, and the 620 bp fragment was isolated. The construct pET-3d-PBC was digested with XbaI, filled-in, then it was digested with ApaI, and the 710 bp fragment was isolated. The three fragments were ligated to create pUR-PB, a plasmid that expressed PBC uricase under the control of osmB promoter and rbs as well as the T7 rbs, which was derived from the pET-3d vector.

The T7 rbs was excised in an additional step. pUR-PB was digested with NcoI, filled-in, then digested with AlwNI, and the 3000 bp fragment was isolated. The plasmid pMFXT133 was digested with NdeI, filled in and then digested with AlwNI, and the 620 bp fragment was isolated. The two fragments were ligated to form pDUR-PB, which expresses PBC under the control of the osmB promoter.

Construction of pOUR-PB-ΔNC

Several changes were introduced into the uricase cDNA, which resulted in a substantial increase in the recombinant enzyme stability. Plasmid pOUR-PBC-ΔNC was constructed, in which the N-terminal six-residue maturation peptide and the tri-peptide at the C-terminus, which function in vivo as peroxysomal targeting signal, were both removed. This was carried out by utilizing PBC sequence in plasmid pDUR-PB and the specific oligonucleotide primers listed in Table 2, using PCR amplification.

TABLE 2

Primers for PCR Amplification of PBC-ANC Uricase
PBC-ΔNC Uricase:

Sense
5' gcgcatATGACTTACAAAAAGAATGATGAGGTAGAG 3'
(SEQ ID NO. 5)

Anti-sense
5' ccgtctagaTTAAGACAACTTCCTCTTGACTGTACCAG
TAATTTTTCCGTATGG 3'
(SEQ ID NO. 6)

The restriction enzyme sequences introduced at the ends of the primers shown in bold and the non-coding regions are shown in lowercase in Table 2. NdeI is sense and XbaI is anti-sense. The anti-sense primer was also used to eliminate an internal NdeI restriction site by introducing a point mutation (underlined) which did not affect the amino acid sequence, and thus, facilitated subcloning by using NdeI.

The 900 base-pair fragment generated by PCR amplification of pDUR-PB was cleaved with NdeI and XbaI and isolated. The obtained fragment was then inserted into a deo expression plasmid pDBAST-RAT-N, which harbors the deo-P1P2 promoter and rbs derived from *E. coli* and constitutively expresses human recombinant insulin precursor. The plasmid was digested with NdeI and XbaI and the 4035 bp fragment was isolated and ligated to the PBC-uricase PCR product. The resulting construct, pDUR-PB-ΔNC, was used to transform *E. coli* K-12 Sϕ733 (F-cytR strA) that expressed a high level of active truncated uricase.

The doubly truncated PBC-ΔNC sequence was also expressed under the control of osmB promoter. The plasmid pDUR-PB-ΔNC was digested with AlwNI-NdeI, and the 3459 bp fragment was isolated. The plasmid pMFXT133, described above, was digested with NdeI-AlwNI, and the 660 bp fragment was isolated. The fragments were then ligated to create pOUR-PB-ΔNC, which was introduced into *E. coli* K-12 strain W3110 F⁻ and expressed high level of active truncated uricase.

Construction of the Uricase Expression Plasmid pOUR-P-ΔN-ks-1

This plasmid was constructed in order to improve the activity and stability of the recombinant enzyme. Pig-KS-ΔN uricase was truncated at the N-terminus only (ΔN), where the six-residue N-terminal maturation peptide was removed, and contained the mutations S46T, R291K and T301S. At position 46, there was a threonine residue instead of serine due to a conservative mutation that occurred during PCR amplification and cloning. At position 291, lysine replaced arginine, and at position 301, serine was inserted instead of threonine. Both were derived from the baboon uricase sequence. The modifications of R291K and T301S are designated KS, and discussed above. The extra lysine residue provided an additional potential PEGylation site.

Figure 4:
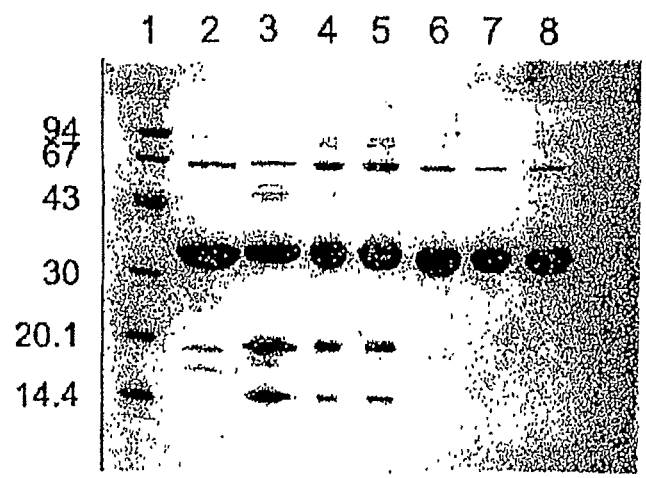
FIG. 4 depicts SDS-PAGE of pig uricase and the highly purified uricase variants produced according to Examples 1-3. The production date (month/year) and the relevant lane number for each sample is indicated in the key below. The Y axis is labeled with the weights of molecular weight markers, and the top of the figure is labeled with the lane numbers. The lanes are as follows: Lane 1—Molecular weight markers; Lane 2—Pig KS-Δ N (7/98); Lane 3—Pig (9/98); Lane 4—Pig KS (6/99); Lane 5—Pig KS (6/99); Lane 6—Pig-Δ (6/99); Lane 7—Pig KS-ΔN (7/99); Lane 8—Pig KS-ΔN (8/99).

To construct pOUR-P-ΔN-ks-1 (FIG. 1), the plasmid pOUR-PB-ΔNC was digested with ApaI-XbaI, and the 3873 bp fragment was isolated. The plasmid pET-3d-PKS (construction shown in FIG. 4) was digested with ApaI-SpeI, and the 270 bp fragment was isolated. SpeI cleavage left a 5'

CTAG extension that was efficiently ligated to DNA fragments generated by XbaI. The two fragments were ligated to create pOUR-P-ΔN-ks-1. After ligation, the SpeI and XbaI recognition sites were lost (their site is shown in parenthesis in FIG. 9). The construct pOUR-P-ΔN-ks-1 was introduced into E. coli K-12 strain W3110 F⁻, prototrophic, ATCC #27325. The resulting Pig-KS-ΔN uricase, expressed under the control of osmB promoter, yielded high levels of recombinant enzyme having superior activity and stability.

FIG. 1 illustrates the structure of plasmid pOUR-P-ΔN-ks-1. Numbers next to restriction sites indicate nucleotide position, relative to HaeII site, designated as 1; restriction sites that were lost during cloning are marked in parenthesis. Plasmid pOUR-P-ΔN-ks-1, encoding Pig-KS-ΔN uricase is 4143 base pairs (bp) long and comprised the following elements:
1. A DNA fragment, 113 bp long, spanning from nucleotide number 1 to NdeI site (at position 113), which includes the osmB promoter and ribosome binding site (rbs).
2. A DNA fragment, 932 bp long, spanning from NdeI (at position 113) to SpeI/XbaI junction (at position 1045), which includes: 900 bp of Pig-KS-ΔN (nucleic acid sequence of amino terminus truncated pig uricase protein in which amino acids 291 and 301 with lysine and serine, respectively, are replaced) coding region and 32 bp flanking sequence derived from pCR™II, from the TA cloning site upstream to the SpeI/XbaI restriction site.
3. A 25 bp multiple cloning sites sequence (MCS) from SpeI/XbaI junction (at position 1045) to HindIII (at position 1070).
4. A synthetic 40 bp oligonucleotide containing the TrpA transcription terminator (ter) with HindIII (at position 1070) and AatII (at position 1110) ends.
5. A DNA fragment, 1519 bp long, spanning from AatII (at position 1110) to MscI/ScaI (at position 2629) sites on pBR322 that includes the tetracycline resistance gene (TetR).
6. A DNA fragment, 1514 bp long, spanning from ScaI (at position 2629) to HaeII (at position 4143) sites on pBR322 that includes the origin of DNA replication.

FIG. 2 shows the DNA and the deduced amino acid sequences of Pig-KS-ΔN uricase. In this figure, the amino acid numbering is according to the complete pig uricase sequence. Following the initiator methionine residue, a threonine was inserted in place of the aspartic acid of the pig uricase sequence. This threonine residue enabled the removal of methionine by bacterial aminopeptidase. The gap in the amino acid sequence illustrates the deleted N-terminal maturation peptide. The restriction sites that were used for the various steps of subcloning of the different uricase sequences (ApaI, NdeI, BamHI, EcoRI and SpeI) are indicated. The 3' untranslated sequence, shown in lowercase letters, was derived from PCR II sequence. The translation stop codon is indicated by an asterisk.

FIG. 3 shows alignment of the amino acid sequences of the various recombinant uricase sequences. The upper line represents the pig uricase, which included the full amino acid sequence. The second line is the sequence of the doubly truncated pig-baboon chimera uricase (PBC-ΔNC). The third line shows the sequence of Pig-KS-ΔN uricase, that is only truncated at the N-terminus and contained the mutations S46T and the amino acid changes R291K and T301 S, both reflecting the baboon origin of the carboxy terminus of the uricase coding sequence. The asterisks indicate the positions in which there are differences in amino acids in the Pig-KS-ΔN as compared to the published pig uricase sequence; the circles indicate positions in which there are differences in amino acids in Pig-KS-ΔN compared to PBC-ΔN, the pig-baboon chimera; and dashed lines indicate deletion of amino acids.

cDNA for native baboon, pig, and rabbit uricase with the Y97H mutation, and the pig/baboon chimera (PBC) were constructed for cloning into E. coli. Clones expressing high levels of the uricase variants were constructed and selected such that all are W3110 F⁻ E. coli, and expression is regulated by osmB. Plasmid DNAs were isolated, verified by DNA sequencing and restriction enzyme analysis, and cells were cultured.

Construction of the truncated uricases, including pig-ΔN and Pig-KS-ΔN was done by cross-ligation between PBC-ΔNC and Pig-KS, following cleavage with restriction endonucleases ApaI and XbaI, and ApaI plus SpeI, respectively. It is reasonable that these truncated mutants would retain activity, since the N-terminal six residues, the "maturation peptide" (1-2), and the C-terminal tri-peptide, "peroxisomal targeting signal" (3-5), do not have functions which significantly affect enzymatic activity, and it is possible that these sequences may be immunogenic. Clones expressing very high levels of the uricase variants were selected.

Example 2

Transformation of the Expression Plasmid into a Bacterial Host Cell

The expression plasmid, pOUR-P-ΔN-ks-1, was introduced into E. coli K-12 strain W3110 F⁻ Bacterial cells were prepared for transformation involved growth to mid log phase in Luria broth (LB), then cells were harvested by centrifugation, washed in cold water, and suspended in 10% glycerol, in water, at a concentration of about $3 \times 10^{10}$ cells per ml. The cells were stored in aliquots, at −70° C. Plasmid DNA was precipitated in ethanol and dissolved in water.

Bacterial cells and plasmid DNA were mixed, and transformation was done by the high voltage electroporation method using Gene Pulser II from BIO-RAD (Trevors et al (1992). Electrotransformation of bacteria by plasmid DNA, in Guide to Electroporation and Electrofusion (D.C. Chang, B. M. Chassy, J. A. Saunders and A. E. Sowers, eds.), pp. 265-290, Academic Press Inc., San Diego, Hanahan et al (1991) Meth. Enzymol., 204, 63-113). Transformed cells were suspended in SOC medium (2% tryptone, 0.5% yeast extract, 10 mM NaCl, 2.5 mM KCl, 10 mM $MgCl_2$, 10 mM $MgSO_4$, 20 mM glucose), incubated, at 37° C., for 1 hour and selected for tetracycline resistance. A high expresser clone was selected.

Example 3

Recombinant Uricase Preparation

Bacteria such as those transformed (see above) were cultured in medium containing glucose; pH was maintained at 7.2±0.2, at approximately 37° C.

Towards the last 5-6 hours of cultivation, the medium was supplemented with KCl to a final concentration of 0.3M. Cultivation was continued to allow uricase accumulation.

Recombinant uricase accumulated within bacterial cells as an insoluble precipitate similar to inclusion bodies (IBs). The cell suspension was washed by centrifugation and suspended in 50 mM Tris buffer, pH 8.0 and 10 mM EDTA and brought to a final volume of approximately 40 times the dry cell weight.

Recombinant uricase-containing IBs, were isolated by centrifugation following disruption of bacterial cells using lysozyme and high pressure. Treatment with lysozyme (2000-3000 units/ml) was done for 16-20 hours at pH 8.0 and 7±3° C., while mixing. The pellet was washed with water and stored at −20° C. until use.

The enriched IBs were further processed after suspending in 50 mM NaHCO$_3$ buffer, pH 10.3±0.1. The suspension was incubated overnight, at room temperature, to allow solubilization of the IB-derived uricase, and subsequently clarified by centrifugation.

Uricase was further purified by several chromatography steps. Initially, chromatography was done on a Q-Sepharose FF column. The loaded column was washed with bicarbonate buffer containing 150 mM NaCl, and uricase was eluted with bicarbonate buffer, containing 250 mM NaCl. Then, Xanthine-agarose resin (Sigma) was used to remove minor impurities from the uricase preparation. The Q-Sepharose FF eluate was diluted with 50 mM glycine buffer, pH 10.3±0.1, to a protein concentration of approximately 0.25 mg/ml and loaded. The column was washed with bicarbonate buffer, pH 10.3±0.1, containing 100 mM NaCl, and uricase was eluted with the same buffer supplemented with 60 μM xanthine. At this stage, the uricase was repurified by Q-Sepharose chromatography to remove aggregated forms.

The purity of each uricase preparation is greater than 95%, as determined by size exclusion chromatography. Less than 0.5% aggregated forms are detected in each preparation using a Superdex 200 column.

Table 3 summarizes purification of Pig-KSΔN uricase from IBs derived from 25 L fermentation broth.

TABLE 3

Purification Of Pig-KSΔN Uricase

| Purification step | Protein (mg) | Activity (U) | Specific Activity (U/mg) |
|---|---|---|---|
| IB dissolution | 12,748 | 47,226 | 3.7 |
| Clarified solution | 11,045 | 44,858 | 4.1 |
| Q-Sepharose I - main pool | 7,590 | 32,316 | 4.3 |
| Xanthine Agarose - main pool | 4,860 | 26,361 | 5.4 |
| Q-Sepahrose II - main pool | 4,438 | 22,982 | 5.2 |
| 30 kD UF retentate | 4,262 | 27,556 | 6.5 |

Example 4

Characteristics of Recombinant Uricases

SDS-PAGE

SDS-PAGE analysis of the highly purified uricase variants (FIG. 4) revealed a rather distinctive pattern. The samples were stored at 4° C., in carbonate buffer, pH 10.3, for up to several months. The full-length variants, Pig, Pig-KS, and PBC, show accumulation of two major degradation products having molecular weights of about 20 and 15 kD. This observation suggests that at least a single nick split the uricase subunit molecule. A different degradation pattern is detected in the amino terminal shortened clones and also in the rabbit uricase, but at a lower proportion. The amino terminus of the rabbit resembles that of the shortened clones. The amino terminal sequences of the uricase fragments generated during purification and storage were determined.

Peptide Sequencing

N-terminal sequencing of bulk uricase preparations was done using the Edman degradation method. Ten cycles were performed. Recombinant Pig uricase (full length clone) generated a greater abundance of degradation fragments compared to Pig-KS-ΔN. The deduced sites of cleavage leading to the degradation fragments are as follows:

1) Major site at position 168 having the sequence: -QSG↓FEGFI-
2) Minor site at position 142 having the sequence: -IRN↓GPPVI- The above sequences do not suggest any known proteolytic cleavage. Nevertheless, cleavage could arise from either proteolysis or some chemical reaction. The amino-truncated uricases are surprisingly more stable than the non-amino truncated uricases. PBCΔNC also had stability similar to the other ΔN molecules and less than non-amino-truncated PBC.

Potency

Activity of uricase was measured by a UV method. Enzymatic reaction rate was determined by measuring the decrease in absorbance at 292 nm resulting from the oxidation of uric acid to allantoin. One activity unit is defined as the quantity of uricase required to oxidize one μmole of uric acid per minute, at 25° C., at the specified conditions. Uricase potency is expressed in activity units per mg protein (U/mg).

The extinction coefficient of 1 mM uric acid at 292 nm is 12.2 mM$^{-1}$ cm$^{-1}$. Therefore, oxidation of 1 μmole of uric acid per ml reaction mixture resulted in a decrease in absorbance of 12.2 mA$_{292}$. The absorbance change with time (ΔA$_{292}$ per minute) was derived from the linear portion of the curve.

Protein concentration was determined using a modified Bradford method (Macart and Gerbaut (1982) *Clin Chim Acta* 122:93-101). The specific activity (potency) of uricase was calculated by dividing the activity in U/ml with protein concentration in mg/ml. The enzymatic activity results of the various recombinant uricases are summarized in Table 4. The results of commercial preparations are included in this table as reference values. It is apparent from these results that truncation of uricase proteins has no significant effect on their enzymatic activity.

TABLE 4

Summary of Kinetic Parameters of Recombinant and Native Uricases

| Uricases | Concentration[1] of Stock(mg/ml) | Specific Activity (U/mg)[2] | Km[4] (μM Uric Acid) | Kcat[5] (1/min) |
|---|---|---|---|---|
| Recombinant | | | | |
| Pig | 0.49 | 7.41 | 4.39 | 905 |
| Pig-ΔN | 0.54 | 7.68 | 4.04 | 822 |
| Pig-KS | 0.33 | 7.16 | 5.27 | 1085 |
| Pig-KS-ΔN | 1.14 | 6.20 | 3.98 | 972 |
| PBC | 0.76 | 3.86 | 4.87 | 662 |
| PBC-ΔNC | 0.55 | 3.85 | 4.3 | 580 |
| Rabbit | 0.44 | 3.07 | 4.14 | 522 |
| Native | | | | |
| Pig (Sigma) | 2.70 | 3.26[3] | 5.85 | 901 |
| A. flavus (Merck) | 1.95 | 0.97[3] | 23.54 | 671 |

Table 4 Notes:
[1]Protein concentration was determined by absorbance measured at 278 nm, using an Extinction coefficient of 11.3 for a 10 mg/ml uricase solution (Mahler, 1963).
[2]1 unit of uricase activity is defined as the amount of enzyme that oxidizes 1 μmole of uric acid to allantoin per minute, at 25° C.
[3]Specific activity values were derived from the Lineweaver-Burk plots, at a concentration of substrate equivalent to 60 μM.
[4] Reaction Mixtures were composed of various combinations of the following stock solutions
100 mM sodium borate buffer, pH 9.2
300 μM Uric acid in 50 mM sodium borate buffer, pH 9.2
1 mg/ml BSA in 50 mM sodium borate buffer, pH 9.2
[5]K$_{cat}$ was calculated by dividing the Vmax (calculated from the respective Lineweaver-Burk plots) by the concentration of uricase in reaction mixture (expressed in mol equivalents, based on the tetrameric molecular weights of the uricases).

Example 5

Conjugation of Uricase with m-PEG (PEGylation)

Pig-KS-ΔN Unease was conjugated using m-PEG-NPC (monomethoxy-poly(ethylene glycol)-nitrophenyl carbonate). Conditions resulting in 2-12 strands of 5, 10, or 20 kD PEG per unease subunit were established. m-PEG-NPC was gradually added to the protein solution. After PEG addition was concluded, the uricase/m-PEG-NPC reaction mixture was then incubated at 2-8° C. for 16-18 hours, until maximal unbound m-PEG strands were conjugated to uricase.

The number of PEG strands per PEG-uricase monomer was determined by Superose 6 size exclusion chromatography (SEC), using PEG and uricase standards. The number of bound PEG strands per subunit was determined by the following equation:

$$\frac{PEG}{\text{strands/subunit}} = \frac{3.42 \times \text{Amount of } PEG \text{ in injected sample } (\mu g)}{\text{Amount of protein in injected sample } (\mu g)}$$

The concentration of PEG and protein moieties in the PEG-uricase sample was determined by size exclusion chromatography (SEC) using ultraviolet (UV) and refractive index (RI) detectors arranged in series (as developed by Kunitani, et al., 1991). Three calibration curves are generated: a protein curve (absorption measured at 220 nm); a protein curve (measured by RI); and PEG curve (measured by RI). Then, the PEG-uricase samples were analyzed using the same system. The resulting UV and RI peak area values of the experimental samples were used to calculate the concentrations of the PEG and protein relative to the calibration curves. The index of 3.42 is the ratio between the molecular weight of uricase monomer (34,192 Daltons) to that of the 10 kD PEG.

Attached PEG improved the solubility of uricase in solutions having physiological pH values. Table 5 provides an indication of the variability between batches of PEGylated Pig-KS-ΔN uricase product. In general, there is an inverse relation between the number of PEG strands attached and retained specific activity (SA) of the enzyme.

TABLE 5

Enzymatic Activity Of PEGylated Pig-KS-ΔN Uricase Conjugates

| Conjugate Batches | PEG MW (kD) | PEG Strands per Uricase Subunit | Uricase SA (U/mg) | SA Percent of Control |
|---|---|---|---|---|
| ΔN-Pig-KS- | — | — | 8.2 | 100 |
| 1-17 # | 5 | 9.7 | 5.8 | 70.4 |
| LP-17 | 10 | 2.3 | 7.8 | 94.6 |
| 1-15 # | 10 | 5.1 | 6.4 | 77.9 |
| 13 # | 10 | 6.4 | 6.3 | 76.9 |
| 14 # | 10 | 6.5 | 6.4 | 77.5 |
| 5-15 # | 10 | 8.8 | 5.4 | 65.3 |
| 5-17 # | 10 | 11.3 | 4.5 | 55.3 |
| 4-17 # | 10 | 11.8 | 4.4 | 53.9 |
| 1-18 # | 20 | 11.5 | 4.5 | 54.4 |

Example 6

PEGylation of Uricase with 1000 D and 100,000 D PEG

Pig-KS-ΔN Uricase was conjugated using 1000 D and 100,000 D m-PEG-NPC as described in Example 5. Conditions resulting in 2-11 strands of PEG per uricase subunit were used. After PEG addition was concluded, the uricase/m-PEG-NPC reaction mixture was then incubated at 2-8° C. for 16-18 hours, until maximal unbound m-PEG strands were conjugated to uricase.

The number of PEG strands per PEG-uricase monomer was determined as described above.

Attached PEG improved the solubility of uricase in solutions having physiological pH values.

Example 7

Pharmacokinetics of Pig-KS-ΔN Uricase Conjugated With PEG

Biological experiments were undertaken in order to determine the optimal extent and size of PEGylation needed to provide therapeutic benefit.

Pharmacokinetic studies in rats, using i.v. injections of 0.4 mg (2 U) per kg body weight of unmodified uricase, administered at day 1 and day 8, yielded a circulating half life of about 10 minutes. However, studies of the clearance rate in rats with 2-11×10 kD PEG-Pig-KS-ΔN uricase, after as many as 9 weekly injections, indicated that clearance did not depend on the number of PEG strands (within this range) and remained relatively constant throughout the study period (see Table 6; with a half-life of about 30 hours). The week-to-week differences are within experimental error. This same pattern is apparent after nine injections of the 10×5 kD PEG, and 10×20 kD PEG-uricase conjugates. The results indicated that regardless of the extent of uricase PEGylation, in this range, similar biological effects were observed in the rat model.

TABLE 6

Half Lives of PEGylated Pig-KS-ΔN Uricase Preparations in Rats

Extent of Modification (PEG Strands per Uricase Subunit)

| Week | 5 kDPEG 10x | 10 kD PEG 2x | 10 kD PEG 5x | 10 kD PEG 7x | 10 kD PEG 9x | 10 kD PEG 11x | 20 kD PEG 10x |
|---|---|---|---|---|---|---|---|
| 1 | 25.7 ± 1.7 (5) | 29.4 ± 3.4 (5) | 37.7 ± 3.1 (5) | 37.6 ± 3.9 (5) | 36.9 ± 4.3 (5) | 31.4 ± 4.3 (5) | 21.6 ± 1.5 (5) |
| 2 | — | — | — | 26.7 ± 3.0 (5) | 28.4 ± 1.6 (5) | — | — |
| 3 | 27.5 ± 3.8 (5) | 29.0 ± 2.6 (5) | 29.9 ± 11.7 (5) | 32.7 ± 11.1 (5) | 26.3 ± 4.7 (5) | 11.8 ± 3.3 (5) | 14.5 ± 2.7 (5) |

TABLE 6-continued

Half Lives of PEGylated Pig-KS-ΔN Uricase Preparations in Rats

Extent of Modification (PEG Strands per Uricase Subunit)

| | 5 kDPEG | 10 kD PEG | | | | | 20 kD PEG |
|---|---|---|---|---|---|---|---|
| Week | 10x | 2x | 5x | 7x | 9x | 11x | 10x |
| 4 | — | — | 27.1 ± 5.3 (5) | 18.4 ± 2.2 (4) | 19.7 ± 5.6 (4) | — | — |
| 5 | 28.6 ± 1.7 (5) | 22.5 ± 2.7 (5) | 34.3 ± 3.9 (4) | 37.3 ± 3.0 (5) | 30.4 ± 3.6 (5) | 30.5 ± 1.3 (5) | 19.3 ± 2.5 (5) |
| 6 | — | — | 35.4 ± 3.1 (14) | 27.1 ± 3.6 (13) | 30.7 ± 2.9 (13) | — | — |
| 7 | 16.5 ± 4.9 (5) | 32.5 ± 4.3 (5) | — | — | — | 16.12 ± 2.7 (5) | 25.8 ± 2.5 (5) |
| 8 | — | — | — | — | — | — | — |
| 9 | 36.8 ± 4.0 (15) | 28.7 ± 2.7 (15) | 34.0 ± 2.4 (13) | 24.2 ± 3.4 (13) | 31.0 ± 2.6 (13) | 29.3 ± 1.4 (15) | 26.7 ± 0.5 (15) |

Table 6 notes: Results are indicated in hours±standard error of the mean. Numbers in parenthesis indicate the number of animals tested.

Rats received weekly i.v. injections of 0.4 mg per kilogram body weight of Pig-KS-ΔN uricase modified as indicated in the table. Each group initially comprised 15 rats, which were alternately bled in subgroups of 5. Several rats died during the study due to the anesthesia. Half-lives were determined by measuring uricase activity (calorimetric assay) in plasma samples collected at 5 minutes, and 6, 24 and 48 hours post injection.

Table 5 describes the batches of PEGylated uricase used in the study.

Bioavailability studies with 6×5 kD PEG-Pig-KS-ΔN uricase in rabbits indicate that, after the first injection, the circulation half-life is 98.2±1.8 hours (i.v.), and the bioavailability after i.m. and subcutaneous (s.c.) injections was 71% and 52%, respectively. However, significant anti-uricase antibody titers were detected, after the second i.m. and s.c. injections, in all of the rabbits, and clearance was accelerated following subsequent injections. Injections of rats with the same conjugate resulted in a half-life of 26±1.6 hours (i.v.), and the bioavailability after i.m. and s.c. injections was 33% and 22%, respectively.

Figure 5:
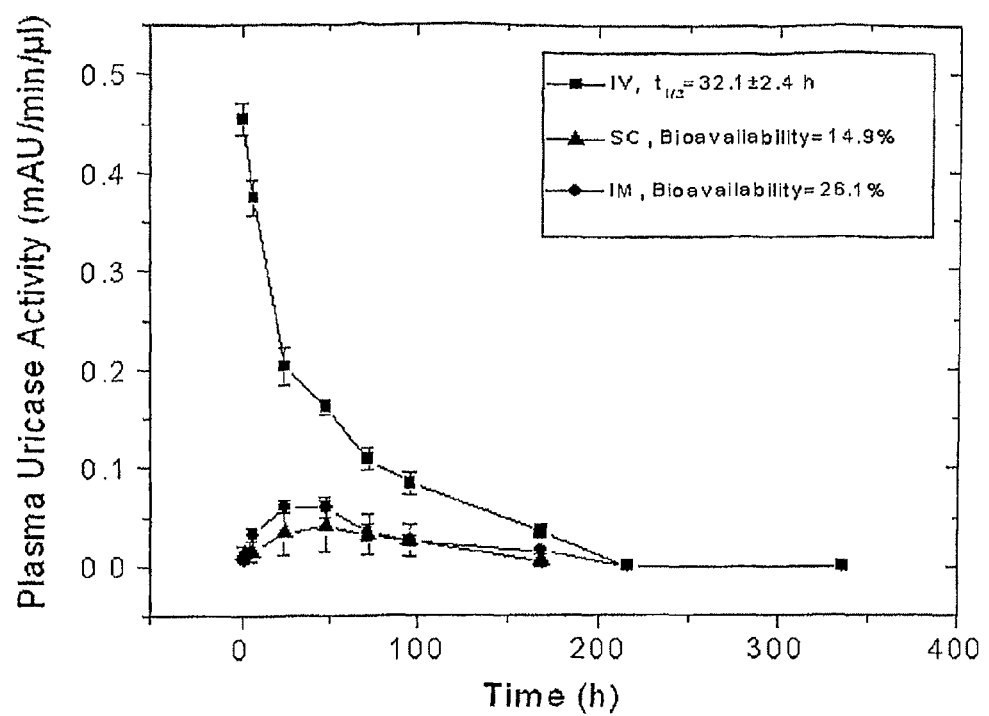
FIG. 5 depicts the pharmacokinetic profiles of PEGylated (9×10 kD) Pig-KS-ΔN uricase in rats following IM (intramuscular), SC (subcutaneous), and IV (intravenous) injections, as determined by monitoring enzymatic activity in blood samples. Uricase activity in plasma samples, which are collected at the indicated time points, is determined using the colorimetric assay. Activity values (mAU=milli-absorbance units) represent the rate of enzymatic reaction per 1 μl of plasma sample. The bioavailability (amount of drug reaching the circulation relative to an IV injection) of uricase injected was calculated from the area under the curve of the graph.

Studies in rats, with 9×10 kD PEG-Pig-KS-ΔN uricase indicate that the circulation half-life after the first injection is 42.4 hours (i.v.), and the bioavailability, after i.m. and s.c. injections, was 28.9% and 14.5%, respectively (see FIG. 5 and Table 7). After the fourth injection, the circulation half-life was 32.1±2.4 hours and the bioavailability, after the i.m. and s.c. injections was 26.1% and 14.9%, respectively.

Figure 6:
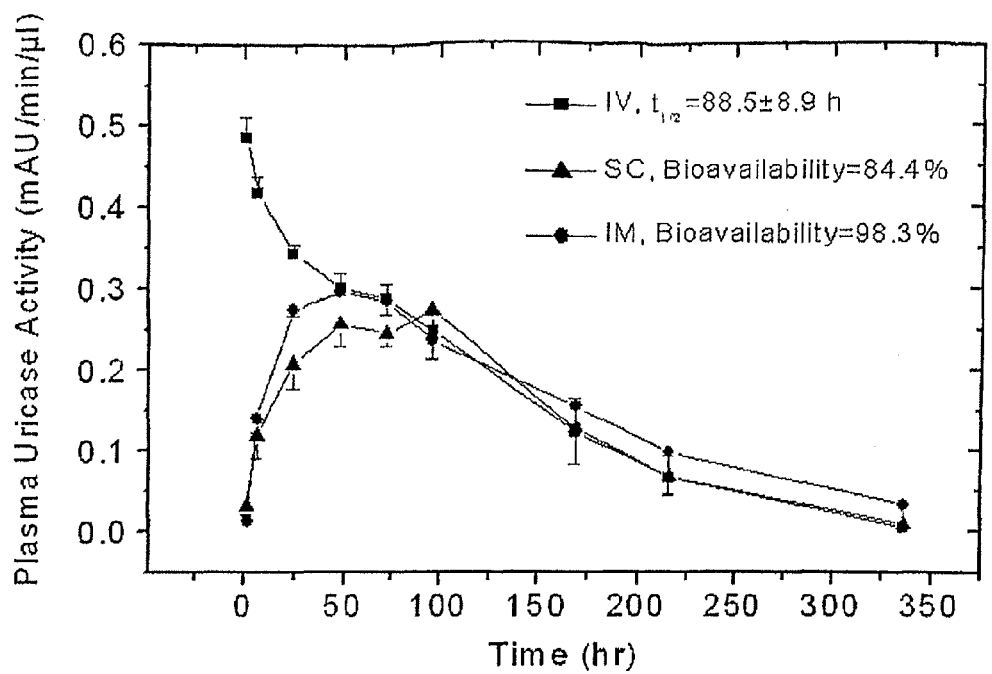
FIG. 6 depicts the pharmacokinetic profiles of PEGylated (9×10 kD) Pig-KS-ΔN uricase in rabbits following IM (intramuscular), SC (subcutaneous), and IV (intravenous) injections, as determined by monitoring enzymatic activity in blood samples. Uricase activity in plasma samples collected at the indicated time points is determined using a colorimetric assay. Activity values (mAU=milli-absorbance units) represent the rate of enzymatic reaction per 1 μl of plasma sample. The bioavailability (amount of drug reaching the circulation relative to an IV injection) of uricase injected was calculated from the area under the curve of the graph.

Similar pharmacokinetic studies, in rabbits, with 9×10 kD PEG-Pig-KS-ΔN uricase indicate that no accelerated clearance was observed following injection of this conjugate (4 biweekly injections were administered). In these animals, the circulation half-life after the first injection was 88.5 hours (i.v.), and the bioavailability, after i.m. and s.c. injections, was 98.3% and 84.4%, respectively (see FIG. 6 and Table 7). After the fourth injection the circulation half-life was 141.1±15.4 hours and the bioavailability, after the i.m. and s.c. injections was 85% and 83%, respectively.

Figure 7:
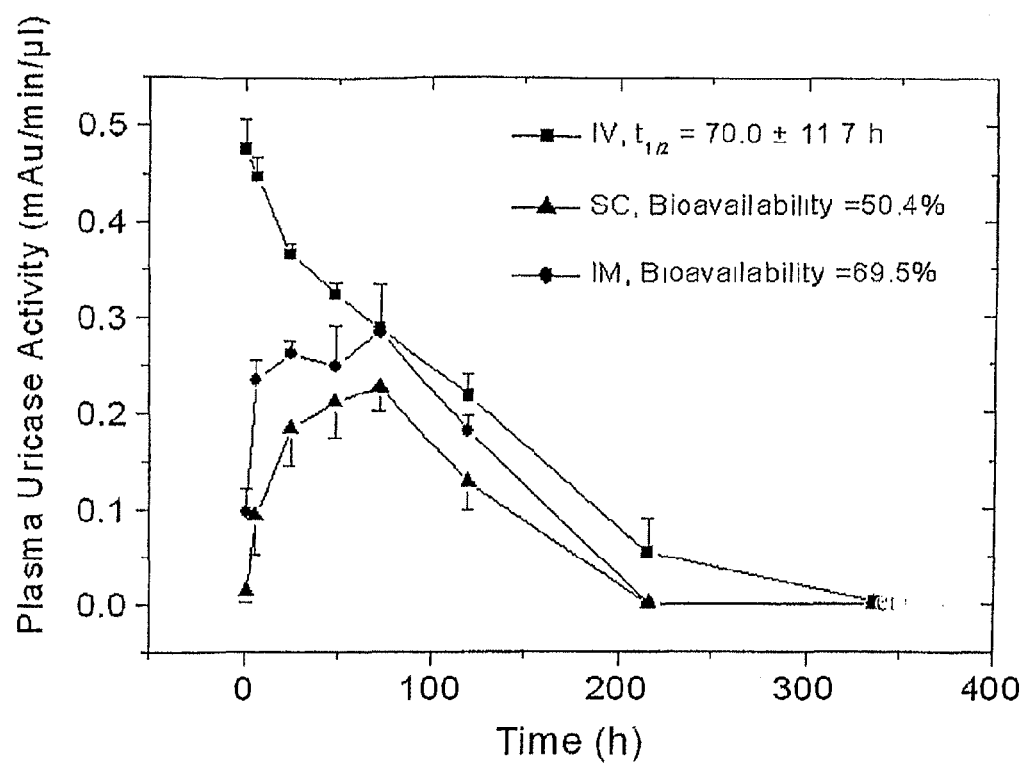
FIG. 7 depicts the pharmacokinetic profiles of PEGylated (9×10 kD) Pig-KS-ΔN uricase in dogs following IM (intramuscular), SC (subcutaneous), and IV (intravenous) injections, as determined by monitoring enzymatic activity in blood samples. Uricase activity in plasma samples, which are collected at the indicated time points, is determined using the calorimetric assay. Activity values (mAU=milli-absorbance units) represent the rate of enzymatic reaction per 1 μl of plasma sample. The bioavailability (amount of drug reaching the circulation relative to an IV injection) of uricase injected was calculated from the area under the curve of the graph.

Similar studies with 9×10 kD PEG-Pig-KS-ΔN were done to assess the bioavailability in beagles (2 males and 2 females in each group). A circulation half-life of 7±11.7 hours was recorded after the first i.v. injection, and the bioavailability, after the i.m. and s.c. injections was 69.5% and 50.4%, respectively (see FIG. 7 and Table 7).

Figure 8:
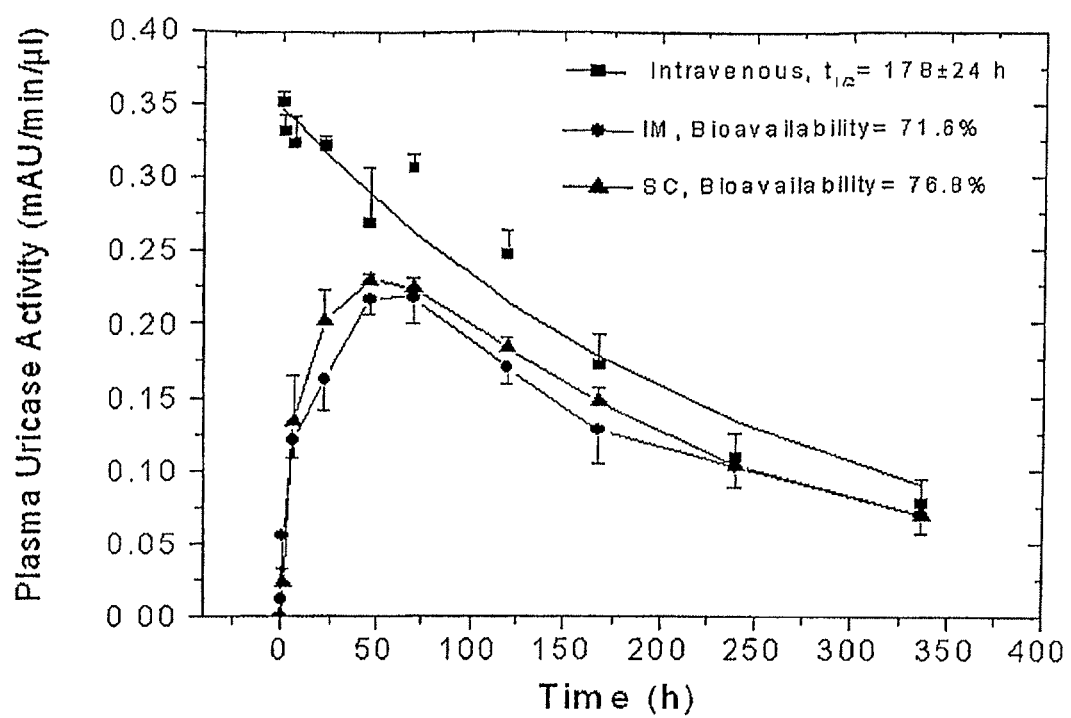
FIG. 8 depicts the pharmacokinetic profiles of PEGylated (9×10 kD) Pig-KS-ΔN uricase in pigs following IM (intramuscular), SC (subcutaneous), and IV (intravenous) injections, as determined by monitoring enzymatic activity in blood samples. Uricase activity in plasma samples, which are collected at the indicated time points, is determined using the colorimetric assay. Activity values (mAU=milli-absorbance units) represent the rate of enzymatic reaction per 1 μl of plasma sample. The bioavailability (amount of drug reaching the circulation relative to an IV injection) of uricase injected was calculated from the area under the curve of the graph.

Studies with 9×10 kD PEG-Pig-KS-ΔN preparations were done using pigs. Three animals per group were used for administration via the i.v., s.c. and i.m. routes. A circulation half-life of 178±24 hours was recorded after the first i.v. injection, and the bioavailability, after the i.m. and s.c. injections was 71.6% and 76.8%, respectively (see FIG. 8 and Table 7).

TABLE 7

Pharmacokinetic Studies with 9 × 10 kD PEG-Pig-KS-ΔN Uricase

| | Half-life (hours) | Bioavailability | |
|---|---|---|---|
| Injection # | i.v. | i.m. | s.c. |
| Rats | | | |
| 1 | 42.4 ± 4.3 | 28.9% | 14.5% |
| 2 | 24.1 ± 5.0 | 28.9% | 14.5% |
| 4 | 32.1 ± 2.4 | 26.1% | 14.9% |
| Rabbits | | | |
| 1 | 88.5 ± 8.9 | 98.3% | 84.4% |
| 2 | 45.7 ± 40.6 | 100% | 100% |
| 4 | 141.1 ± 15.4 | 85% | 83% |
| Dogs | | | |
| 1 | 70.0 ± 11.7 | 69.5% | 50.4% |
| Pigs | | | |
| 1 | 178 ± 24 | 71.6% | 76.8% |

Absorption, distribution, metabolism, and excretion (ADME) studies were done after iodination of 9×10 kD PEG-Pig-KS-ΔN uricase by the Bolton & Hunter method with $^{125}$I. The labeled conjugate was injected into 7 groups of 4 rats each (2 males and 2 females). Distribution of radioactivity was analyzed after 1 hour and every 24 hours for 7 days (except day 5). Each group, in its turn, was sacrificed and the different organs were excised and analyzed. The seventh group was kept in a metabolic cage, from which the urine and feces were collected. The distribution of the material throughout the animal's body was evaluated by measuring the total radioactivity in each organ, and the fraction of counts (kidney, liver, lung, and spleen) that were available for precipitation with TCA (i.e. protein bound, normalized to the organ size). Of the organs that were excised, none had a higher specific radioactivity than the others, thus no significant accumulation was seen for instance in the liver or kidney. 70% of the radioactivity was excreted by day 7.

Example 8

Clinical Trial Results

A randomized, open-label, multicenter, parallel group study was performed to assess the urate response, and pharmacokinetic and safety profiles of PEG-uricase (Puricase®, Savient Pharmaceuticals) in human patients with hyperuricemia and severe gout who were unresponsive to or intolerant of conventional therapy. The mean duration of disease was 14 years and 70 percent of the study population had one or more tophi.

In the study, 41 patients (mean age of 58.1 years) were randomized to 12 weeks of treatment with intravenous PEG-uricase at one of four dose regimens: 4 mg every two weeks (7 patients); 8 mg every two weeks (8 patients); 8 mg every four weeks (13 patients); or 12 mg every four weeks (13 patients). Plasma uricase activity and urate levels were measured at defined intervals. Pharmacokinetic parameters, mean plasma urate concentration and the percentage of time that plasma urate was less than or equal to 6 mg/dL were derived from analyses of the uricase activities and urate levels.

Patients who received 8 mg of PEG-uricase every two weeks had the greatest reduction in PUA with levels below 6 mg/dL 92 percent of the treatment time (pre-treatment plasma urate of 9.1 mg/dL vs. mean plasma urate of 1.4 mg/dL over 12 weeks).

Substantial and sustained lower plasma urate levels were also observed in the other PEG-uricase treatment dosing groups: PUA below 6 mg/ml 86 percent of the treatment time in the 8 mg every four weeks group (pre-treatment plasma urate of 9.1 mg/dL vs. mean plasma urate of 2.6 mg/dL over 12 weeks); PUA below 6 mg/ml 84 percent of the treatment time in the 12 mg every four weeks group (pre-treatment plasma urate of 8.5 mg/dL vs. mean plasma urate of 2.6 mg/dL over 12 weeks); and PUA below 6 mg/ml 73 percent of the treatment time in the 4 mg every two weeks group (pre-treatment plasma urate of 7.6 mg/dL vs. mean plasma urate of 4.2 mg/dL over 12 weeks).

The maximum percent decrease in plasma uric acid from baseline within the first 24 hours of PEG-uricase dosing was 72% for subjects receiving 4 mg/2 weeks (p equals 0.0002); 94% for subjects receiving 8 mg/2 weeks (p less than 0.0001); 87% for subjects receiving 8 mg/4 weeks (p less than 0.0001); and 93% for subjects receiving 12 mg/4 weeks (p less than 0.0001).

The percent decrease in plasma uric acid from baseline over the 12-week treatment period was 38% for subjects receiving 4 mg/2 weeks (p equals 0.0002); 86% for subjects receiving 8 mg/2 weeks (p less than 0.0001); 58% for subjects receiving 8 mg/4 weeks (p equals 0.0003); and 67% for subjects receiving 12 mg/4 weeks (p less than 0.0001).

Surprisingly, some subjects receiving PEG-uricase experienced an infusion related adverse event, i.e., an infusion reaction. These reactions occurred in 14% of the total infusions.

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

---

We claim:

1. A method for producing a uricase comprising the steps of:
   (i) culturing a host cell comprising a vector comprising a nucleic acid sequence encoding a uricase comprising a mammalian uricase amino acid sequence truncated at the amino terminus or the carboxy terminus or both the amino and carboxy termini by 1-6 amino acids and further comprising an amino acid substitution with threonine at position 7 (D7T), an amino acid substitution at position 46 (S46T), an amino acid substitution with lysine at position 291 (R291K) and an amino acid substitution with serine at position 301 (T301S), said truncation and amino acid substitution being relative to an amino acid sequence of SEQ ID NO:11;
   wherein the nucleic acid sequence is operatively linked to a heterologous promoter under conditions such that the nucleic acid sequence is expressed by the host cell; and
   (ii) isolating the expressed uricase.

2. The method of claim 1, wherein the expressed uricase comprises an amino terminal amino acid selected from alanine, glycine, proline, serine, or threonine.

3. The method of claim 1, wherein the expressed uricase comprises an amino terminal threonine.

4. The method of claim 1, wherein the expressed uricase comprises an amino terminal methionine.

5. The method of claim 1, wherein the uricase is conjugated with a polymer.

6. The method of claim 1, wherein the heterologous promoter is an osmB promoter.

7. The method of claim 3, wherein the expressed uricase consists of the amino acid sequence of SEQ ID NO: 8.

8. The method of claim 3, wherein the expressed uricase comprises the amino acid sequence of SEQ ID NO: 8.

9. The method of claim 4, wherein the expressed uricase consists of the amino acid sequence of SEQ ID NO: 7.

10. The method of claim 4, wherein the expressed uricase comprises the amino acid sequence of SEQ ID NO: 7.

11. The method of claim 5, wherein the polymer is selected from the group consisting of poly(ethylene glycol), dextran, polypropylene glycol, hydroxypropylmethyl cellulose, carboxymethylcellulose, polyvinyl pyrrolidone and polyvinyl alcohol.

12. The method of claim 5, wherein the uricase is a polyethylene glycol—uricase conjugate.

13. The method of claim 12, wherein the conjugate comprises 2 to 12 polyethylene glycol molecules on each uricase subunit.

14. The method of claim 12, wherein each polyethylene glycol molecule has a molecular weight between about 1 kD and 100 kD.

15. The method of claim 13, wherein each polyethylene glycol molecule has a molecular weight between 1 kD and 50 kD.

16. The method of claim 13, wherein each polyethylene glycol molecule has a molecular weight between 5 kD and 20 kD.

17. The method of claim 13, wherein each polyethylene glycol molecule has a molecular weight of 10 kD.

* * * * *